(12) United States Patent
Stack et al.

(10) Patent No.: US 9,844,453 B2
(45) Date of Patent: Dec. 19, 2017

(54) POSITIONING TOOLS AND METHODS FOR IMPLANTING MEDICAL DEVICES

(71) Applicant: Boston Scientific Scimed, Inc., Maple Grove, MN (US)

(72) Inventors: Richard S. Stack, Chapel Hill, NC (US); Richard A. Glenn, Santa Rosa, CA (US); Daniel Balbierz, Redwood City, CA (US); John Lunsford, San Carlos, CA (US); William L. Athas, Durham, NC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/878,791

(22) Filed: Oct. 8, 2015

(65) Prior Publication Data

US 2016/0022464 A1 Jan. 28, 2016

Related U.S. Application Data

(60) Continuation of application No. 14/305,255, filed on Jun. 16, 2014, now Pat. No. 9,180,036, which is a
(Continued)

(51) Int. Cl.
*A61M 29/00* (2006.01)
*A61F 5/00* (2006.01)

(52) U.S. Cl.
CPC .......... *A61F 5/0089* (2013.01); *A61F 5/0079* (2013.01)

(58) Field of Classification Search
CPC . A61F 5/0089; A61F 5/0079; A61M 25/0074; A61M 25/04; A61M 25/10
(Continued)

(56) References Cited

U.S. PATENT DOCUMENTS

| 1,408,865 | A | | 3/1922 | Codwell | |
| 1,433,031 | A | * | 10/1922 | Pegaitaz | A61M 29/02 606/198 |

(Continued)

FOREIGN PATENT DOCUMENTS

| CH | 680263 A5 | 7/1992 |
| DE | 08708978 U1 | 11/1987 |

(Continued)

OTHER PUBLICATIONS

US 8,668,662, 03/2014, Levine et al. (withdrawn)
(Continued)

*Primary Examiner* — Alvin Stewart
(74) *Attorney, Agent, or Firm* — Bookoff McAndrews, PLLC

(57) ABSTRACT

Described herein is a positioning tool having an elongate portion for carrying a medical implant. Also described is a method of positioning a medical implant using an elongate positioning tool. One form of the method includes positioning a medical implant on a distal portion of an elongate positioning tool, inserting the positioning tool with the implant thereon into a body cavity manipulating the positioning tool to position the implant into contact with tissue at an attachment location, attaching the implant to surrounding tissue at the attachment location, separating the implant from the positioning tool, and withdrawing the positioning tool from the body. In a preferred embodiment, the position of the implant is visually confirmed using an endoscope before the implant is attached to surrounding tissue. In one embodiment, the implant is a satiation device and the body cavity is the esophagus and/or stomach. In an alternative embodiment, an expansion structure on the distal end of the elongate portion expands and/or contracts the medical implant to facilitate positioning.

5 Claims, 13 Drawing Sheets

Related U.S. Application Data continuation of application No. 13/032,569, filed on Feb. 22, 2011, now Pat. No. 8,784,354, which is a continuation of application No. 11/479,204, filed on Jun. 30, 2006, now Pat. No. 7,892,292, which is a division of application No. 10/345,698, filed on Jan. 16, 2003, now Pat. No. 7,097,665, and a continuation-in-part of application No. 10/751,751, filed on Jan. 5, 2004, now Pat. No. 7,981,162, which is a division of application No. 10/118,289, filed on Apr. 8, 2002, now Pat. No. 6,845,776, which is a continuation-in-part of application No. 09/940,110, filed on Aug. 27, 2001, now Pat. No. 6,675,809.

(58) Field of Classification Search
USPC ........................................ 623/23.65; 606/198
See application file for complete search history.

(56) References Cited

U.S. PATENT DOCUMENTS

| | | | |
|---|---|---|---|
| 3,663,965 A | 5/1972 | Lee et al. | |
| 3,667,474 A * | 6/1972 | Lapkin | A61M 29/02 |
| | | | 606/198 |
| 4,043,338 A * | 8/1977 | Homm | A61M 31/00 |
| | | | 604/105 |
| 4,134,405 A | 1/1979 | Smit | |
| 4,207,890 A | 6/1980 | Mamajek et al. | |
| 4,246,893 A | 1/1981 | Berson | |
| 4,315,509 A | 2/1982 | Smit | |
| 4,331,277 A | 5/1982 | Green | |
| 4,403,604 A | 9/1983 | Wilkinson et al. | |
| 4,416,267 A | 11/1983 | Garren et al. | |
| 4,417,360 A | 11/1983 | Moasser | |
| 4,441,215 A | 4/1984 | Kaster | |
| 4,467,804 A | 8/1984 | Hardy et al. | |
| 4,485,805 A | 12/1984 | Foster, Jr. | |
| 4,501,264 A | 2/1985 | Rockey | |
| 4,585,000 A * | 4/1986 | Hershenson | A61M 29/02 |
| | | | 604/108 |
| 4,607,618 A | 8/1986 | Angelchik | |
| 4,617,932 A | 10/1986 | Kornberg | |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,747,849 A | 5/1988 | Galitier | |
| 4,846,836 A | 7/1989 | Reich | |
| 4,848,367 A | 7/1989 | Avant et al. | |
| 4,899,747 A | 2/1990 | Garren et al. | |
| 4,925,446 A | 5/1990 | Garay et al. | |
| 4,946,440 A | 8/1990 | Hall | |
| 4,969,896 A | 11/1990 | Shors | |
| 4,997,084 A | 3/1991 | Opie et al. | |
| 5,006,106 A | 4/1991 | Angelchik | |
| 5,037,021 A | 8/1991 | Mills et al. | |
| 5,061,275 A | 10/1991 | Wallsten et al. | |
| 5,084,061 A | 1/1992 | Gau et al. | |
| 5,088,979 A | 2/1992 | Filipi et al. | |
| 5,113,846 A * | 5/1992 | Hiltebrandt | A61B 1/32 |
| | | | 600/225 |
| 5,163,952 A | 11/1992 | Froix | |
| 5,211,658 A | 5/1993 | Clouse | |
| 5,234,454 A | 8/1993 | Bangs | |
| 5,246,456 A | 9/1993 | Wilkinson | |
| 5,259,399 A | 11/1993 | Brown | |
| 5,263,629 A | 11/1993 | Trumbull et al. | |
| 5,275,610 A | 1/1994 | Eberbach | |
| 5,279,565 A * | 1/1994 | Klein | A61M 25/007 |
| | | | 604/105 |
| 5,290,217 A | 3/1994 | Campos | |
| 5,306,300 A | 4/1994 | Berry | |
| 5,314,473 A | 5/1994 | Godin | |
| 5,327,914 A | 7/1994 | Shlain | |
| 5,345,949 A | 9/1994 | Shlain | |
| 5,355,897 A | 10/1994 | Pietrafitta et al. | |
| 5,401,241 A | 3/1995 | Delany | |
| 5,403,326 A | 4/1995 | Harrison et al. | |
| 5,405,377 A | 4/1995 | Cragg | |
| 5,431,673 A | 7/1995 | Summers et al. | |
| 5,443,477 A * | 8/1995 | Marin | A61F 2/95 |
| | | | 604/106 |
| 5,486,187 A | 1/1996 | Schenck | |
| 5,514,176 A | 5/1996 | Bosley, Jr. | |
| 5,535,935 A | 7/1996 | Vidal et al. | |
| 5,542,949 A | 8/1996 | Yoon | |
| 5,562,239 A | 10/1996 | Boiarski et al. | |
| 5,571,116 A | 11/1996 | Bolanos et al. | |
| 5,577,654 A | 11/1996 | Bishop | |
| 5,591,196 A * | 1/1997 | Marin | A61F 2/95 |
| | | | 604/106 |
| 5,593,434 A | 1/1997 | Williams | |
| 5,597,107 A | 1/1997 | Knodel et al. | |
| 5,609,624 A | 3/1997 | Kalis | |
| 5,618,300 A | 4/1997 | Marin et al. | |
| 5,628,786 A | 5/1997 | Banas et al. | |
| 5,630,539 A | 5/1997 | Plyley et al. | |
| 5,647,526 A | 7/1997 | Green et al. | |
| 5,653,743 A | 8/1997 | Martin | |
| 5,662,713 A | 9/1997 | Andersen et al. | |
| 5,673,841 A | 10/1997 | Schulze et al. | |
| 5,674,241 A | 10/1997 | Bley et al. | |
| 5,706,998 A | 1/1998 | Plyley et al. | |
| 5,709,657 A | 1/1998 | Zimmon | |
| 5,713,907 A * | 2/1998 | Hogendijk | A61F 2/95 |
| | | | 606/108 |
| 5,720,776 A | 2/1998 | Chuter et al. | |
| 5,749,918 A | 5/1998 | Hogendijk et al. | |
| 5,755,661 A * | 5/1998 | Schwartzman | A61B 17/02 |
| | | | 600/204 |
| 5,762,255 A | 6/1998 | Chrisman et al. | |
| 5,771,903 A | 6/1998 | Jakobsson | |
| 5,776,141 A * | 7/1998 | Klein | A61F 2/958 |
| | | | 606/195 |
| 5,785,684 A | 7/1998 | Zimmon | |
| 5,792,119 A | 8/1998 | Marx | |
| 5,820,584 A | 10/1998 | Crabb | |
| 5,839,639 A | 11/1998 | Sauer et al. | |
| 5,848,964 A | 12/1998 | Samuels | |
| 5,855,311 A | 1/1999 | Hamblin et al. | |
| 5,855,565 A * | 1/1999 | Bar-Cohen | A61M 29/02 |
| | | | 604/104 |
| 5,855,601 A | 1/1999 | Bessler et al. | |
| 5,856,445 A | 1/1999 | Korsmeyer | |
| 5,861,036 A | 1/1999 | Godin | |
| 5,868,141 A | 2/1999 | Ellias | |
| 5,887,594 A | 3/1999 | LoCicero, III | |
| 5,897,562 A | 4/1999 | Bolanos et al. | |
| 5,910,144 A | 6/1999 | Hayashi et al. | |
| 5,922,019 A | 7/1999 | Hankh et al. | |
| 5,947,983 A | 9/1999 | Solar et al. | |
| 5,993,473 A | 11/1999 | Chan et al. | |
| 5,993,483 A | 11/1999 | Gianotti | |
| 6,013,019 A * | 1/2000 | Fischell | A61F 2/95 |
| | | | 600/1 |
| 6,016,848 A | 1/2000 | Egrees | |
| 6,030,406 A * | 2/2000 | Davis | A61B 17/00008 |
| | | | 604/104 |
| 6,051,015 A | 4/2000 | Maahs | |
| 6,086,600 A | 7/2000 | Kortenbach | |
| 6,098,629 A | 8/2000 | Johnson et al. | |
| 6,102,922 A | 8/2000 | Jakobsson et al. | |
| 6,113,609 A | 9/2000 | Adams | |
| 6,120,534 A | 9/2000 | Ruiz | |
| 6,126,058 A | 10/2000 | Adams et al. | |
| 6,146,416 A | 11/2000 | Andersen et al. | |
| 6,159,146 A | 12/2000 | El Gazayerli | |
| 6,159,238 A | 12/2000 | Killion et al. | |
| 6,168,616 B1 * | 1/2001 | Brown, III | A61F 2/86 |
| | | | 606/108 |
| 6,174,316 B1 * | 1/2001 | Tuckey | A61F 2/958 |
| | | | 606/108 |

(56) References Cited

U.S. PATENT DOCUMENTS

| | | | |
|---|---|---|---|
| 6,179,195 B1 | 1/2001 | Adams et al. | |
| 6,197,022 B1 | 3/2001 | Baker | |
| 6,206,930 B1 | 3/2001 | Burg et al. | |
| 6,217,585 B1 * | 4/2001 | Houser | A61F 2/958 606/108 |
| 6,245,088 B1 | 6/2001 | Lowery | |
| 6,251,132 B1 | 6/2001 | Ravenscroft et al. | |
| 6,254,642 B1 | 7/2001 | Taylor | |
| 6,258,120 B1 | 7/2001 | McKenzie et al. | |
| 6,264,700 B1 | 7/2001 | Kilcoyne et al. | |
| 6,287,334 B1 | 9/2001 | Moll et al. | |
| 6,290,674 B1 * | 9/2001 | Roue | A61B 17/00234 604/107 |
| 6,302,917 B1 | 10/2001 | Dua et al. | |
| 6,319,251 B1 * | 11/2001 | Tu | A61B 18/1492 606/194 |
| 6,355,051 B1 * | 3/2002 | Sisskind | A61F 2/013 606/200 |
| 6,358,197 B1 | 3/2002 | Silverman et al. | |
| 6,416,522 B1 | 7/2002 | Strecker | |
| 6,425,916 B1 | 7/2002 | Garrison et al. | |
| 6,436,088 B2 * | 8/2002 | Frazier | A61F 2/95 604/500 |
| 6,454,785 B2 | 9/2002 | De Hoyos Garza | |
| 6,460,543 B1 | 10/2002 | Forsell | |
| 6,461,346 B1 * | 10/2002 | Buelna | A61M 25/10 604/104 |
| 6,461,366 B1 | 10/2002 | Seguin | |
| 6,468,298 B1 * | 10/2002 | Pelton | A61F 2/95 606/194 |
| 6,494,888 B1 | 12/2002 | Laufer et al. | |
| 6,494,895 B2 | 12/2002 | Addis | |
| 6,503,264 B1 | 1/2003 | Birk | |
| 6,506,196 B1 | 1/2003 | Laufer et al. | |
| 6,527,784 B2 | 3/2003 | Adams et al. | |
| 6,537,247 B2 * | 3/2003 | Shannon | A61M 25/104 604/103.05 |
| 6,540,789 B1 | 4/2003 | Silverman et al. | |
| 6,544,291 B2 | 4/2003 | Taylor | |
| 6,547,801 B1 | 4/2003 | Dargent et al. | |
| 6,558,400 B2 | 5/2003 | Deem et al. | |
| 6,558,429 B2 | 5/2003 | Taylor | |
| 6,572,627 B2 | 6/2003 | Gabbay | |
| 6,572,629 B2 | 6/2003 | Kalloo | |
| 6,575,896 B2 | 6/2003 | Silverman et al. | |
| 6,579,302 B2 * | 6/2003 | Duerig | A61B 17/3207 606/198 |
| 6,582,451 B1 * | 6/2003 | Marucci | A61B 17/29 606/207 |
| 6,592,596 B1 | 7/2003 | Geitz et al. | |
| 6,596,023 B1 | 7/2003 | Nunez et al. | |
| 6,607,555 B2 | 8/2003 | Patterson et al. | |
| 6,627,206 B2 | 9/2003 | Lloyd | |
| 6,632,227 B2 | 10/2003 | Adams | |
| 6,663,639 B1 | 12/2003 | Laufer et al. | |
| 6,675,809 B2 | 1/2004 | Stack et al. | |
| 6,676,692 B2 * | 1/2004 | Rabkin | A61F 2/95 604/104 |
| 6,740,098 B2 | 5/2004 | Abrams et al. | |
| 6,740,105 B2 * | 5/2004 | Yodfat | A61F 2/958 606/198 |
| 6,740,121 B2 | 5/2004 | Geitz et al. | |
| 6,746,460 B2 | 6/2004 | Gannoe et al. | |
| 6,755,869 B2 | 6/2004 | Geitz | |
| 6,764,518 B2 | 7/2004 | Godin | |
| 6,773,440 B2 | 8/2004 | Gannoe et al. | |
| 6,773,441 B1 | 8/2004 | Laufer et al. | |
| 6,790,214 B2 | 9/2004 | Kraemer et al. | |
| 6,790,237 B2 | 9/2004 | Stinson | |
| 6,793,668 B1 * | 9/2004 | Fisher | A61F 2/013 604/105 |
| 6,821,285 B2 | 11/2004 | Laufer et al. | |
| 6,835,200 B2 | 12/2004 | Laufer et al. | |
| 6,845,776 B2 | 1/2005 | Stack et al. | |
| 6,916,332 B2 | 7/2005 | Adams | |
| 6,921,361 B2 | 7/2005 | Suzuki et al. | |
| 6,932,838 B2 | 8/2005 | Schwartz et al. | |
| 6,960,233 B1 | 11/2005 | Berg et al. | |
| 6,966,875 B1 | 11/2005 | Longobardi | |
| 6,981,978 B2 | 1/2006 | Gannoe | |
| 6,981,980 B2 | 1/2006 | Sampson et al. | |
| 6,994,715 B2 | 2/2006 | Gannoe et al. | |
| 7,011,094 B2 | 3/2006 | Rapackie et al. | |
| 7,020,531 B1 | 3/2006 | Colliu et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,056,305 B2 | 6/2006 | Garza | |
| 7,066,945 B2 | 6/2006 | Hashiba et al. | |
| 7,070,598 B2 * | 7/2006 | Lim | A61B 17/025 606/99 |
| 7,083,629 B2 | 8/2006 | Weller et al. | |
| 7,090,699 B2 | 8/2006 | Geitz | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,112,186 B2 | 9/2006 | Shah | |
| 7,120,498 B2 | 10/2006 | Imran et al. | |
| 7,121,283 B2 | 10/2006 | Stack et al. | |
| 7,146,984 B2 | 12/2006 | Stack et al. | |
| 7,147,140 B2 | 12/2006 | Wukusick et al. | |
| 7,152,607 B2 | 12/2006 | Stack et al. | |
| 7,153,314 B2 | 12/2006 | Laufer et al. | |
| 7,160,312 B2 | 1/2007 | Saadat et al. | |
| 7,172,613 B2 | 2/2007 | Wazne | |
| 7,175,638 B2 | 2/2007 | Gannoe et al. | |
| 7,175,660 B2 | 2/2007 | Cartledge et al. | |
| 7,211,114 B2 | 5/2007 | Bessler et | |
| 7,214,233 B2 | 5/2007 | Gannoe et al. | |
| 7,220,237 B2 | 5/2007 | Gannoe et al. | |
| 7,220,284 B2 | 5/2007 | Kagan et al. | |
| 7,223,277 B2 | 5/2007 | DeLegge | |
| 7,229,428 B2 | 6/2007 | Gannoe et al. | |
| 7,229,453 B2 | 6/2007 | Anderson et al. | |
| 7,255,675 B2 | 8/2007 | Gertner et al. | |
| 7,258,696 B2 * | 8/2007 | Rabkin | A61F 2/95 606/191 |
| 7,261,722 B2 | 8/2007 | McGuckin, Jr. et al. | |
| 7,288,101 B2 | 10/2007 | Deem et al. | |
| 7,306,614 B2 | 12/2007 | Weller et al. | |
| 7,315,509 B2 | 1/2008 | Jeong et al. | |
| 7,316,716 B2 | 1/2008 | Egan | |
| 7,320,696 B2 | 1/2008 | Gazi et al. | |
| 7,326,207 B2 | 2/2008 | Edwards | |
| 7,335,210 B2 | 2/2008 | Smit | |
| 7,347,863 B2 | 3/2008 | Rothe et al. | |
| 7,347,875 B2 | 3/2008 | Levine et al. | |
| 7,354,454 B2 | 4/2008 | Stack et al. | |
| 7,399,304 B2 | 7/2008 | Gambale et al. | |
| 7,431,725 B2 | 10/2008 | Stack et al. | |
| 7,461,767 B2 | 12/2008 | Viola et al. | |
| 7,470,251 B2 | 12/2008 | Shah | |
| 7,485,142 B2 | 2/2009 | Milo | |
| 7,503,922 B2 | 3/2009 | Deem et al. | |
| 7,520,884 B2 | 4/2009 | Swanstrom et al. | |
| 7,575,586 B2 | 8/2009 | Berg et al. | |
| 7,597,704 B2 * | 10/2009 | Frazier | A61B 17/12022 606/213 |
| 7,608,114 B2 | 10/2009 | Levine et al. | |
| 7,615,064 B2 | 11/2009 | Bjerken | |
| 7,625,377 B2 * | 12/2009 | Veldhuizen | A61F 2/44 606/105 |
| 7,628,821 B2 | 12/2009 | Stack et al. | |
| 7,662,161 B2 | 2/2010 | Briganti et al. | |
| 7,670,279 B2 | 3/2010 | Gertner | |
| 7,674,271 B2 | 3/2010 | Bjerken | |
| 7,695,446 B2 | 4/2010 | Levine et al. | |
| 7,708,181 B2 | 5/2010 | Cole et al. | |
| 7,717,843 B2 | 5/2010 | Balbierz et al. | |
| 7,721,932 B2 | 5/2010 | Cole et al. | |
| 7,731,757 B2 | 6/2010 | Taylor et al. | |

(56) References Cited

U.S. PATENT DOCUMENTS

| | | | |
|---|---|---|---|
| 7,735,493 B2 * | 6/2010 | van der Burg | A61B 17/0057 128/887 |
| 7,744,613 B2 | 6/2010 | Ewers et al. | |
| 7,744,627 B2 | 6/2010 | Orban et al. | |
| 7,753,870 B2 | 7/2010 | Demarais et al. | |
| 7,763,028 B2 * | 7/2010 | Lim | A61B 17/025 606/105 |
| 7,763,074 B2 * | 7/2010 | Altarac | A61B 17/7065 606/90 |
| 7,766,861 B2 | 8/2010 | Levine et al. | |
| 7,771,382 B2 | 8/2010 | Levine et al. | |
| 7,794,447 B2 | 9/2010 | Dann et al. | |
| 7,819,836 B2 | 10/2010 | Levine et al. | |
| 7,837,645 B2 | 11/2010 | Bessler et al. | |
| 7,846,138 B2 | 12/2010 | Dann et al. | |
| 7,846,174 B2 | 12/2010 | Baker et al. | |
| 7,881,797 B2 | 2/2011 | Griffin et al. | |
| 7,892,214 B2 | 2/2011 | Kagan et al. | |
| 7,892,292 B2 | 2/2011 | Stack et al. | |
| 7,901,409 B2 * | 3/2011 | Canaveral | A61B 17/8858 600/222 |
| 8,029,455 B2 | 10/2011 | Stack et al. | |
| 8,038,720 B2 | 10/2011 | Wallace et al. | |
| 8,057,420 B2 | 11/2011 | Meade et al. | |
| 8,118,827 B2 * | 2/2012 | Duerig | A61B 17/3207 604/107 |
| 8,282,598 B2 | 10/2012 | Belhe et al. | |
| 8,317,798 B2 * | 11/2012 | Lim | A61B 17/025 606/105 |
| 8,475,401 B2 | 7/2013 | Priplata et al. | |
| 8,517,972 B2 | 8/2013 | Graham et al. | |
| 8,535,259 B2 | 9/2013 | Thompson | |
| 8,568,488 B2 | 10/2013 | Stack et al. | |
| 8,574,184 B2 | 11/2013 | Errico et al. | |
| 8,579,849 B2 | 11/2013 | Grau et al. | |
| 8,591,452 B2 | 11/2013 | Priplata et al. | |
| 8,597,224 B2 | 12/2013 | Vargas | |
| 8,801,746 B1 * | 8/2014 | Kreidler | A61F 2/01 606/200 |
| 9,259,267 B2 * | 2/2016 | Forde | A61B 18/1492 |
| 9,282,973 B2 * | 3/2016 | Hughett, Sr. | A61B 17/1227 |
| 9,314,249 B2 * | 4/2016 | Kreidler | A61B 17/12122 |
| 2001/0002411 A1 | 5/2001 | Ronan et al. | |
| 2001/0011543 A1 | 8/2001 | Forsell | |
| 2001/0020189 A1 | 9/2001 | Taylor | |
| 2001/0020190 A1 | 9/2001 | Taylor | |
| 2001/0021796 A1 | 9/2001 | Silverman et al. | |
| 2001/0044595 A1 | 11/2001 | Reydel et al. | |
| 2002/0022851 A1 | 2/2002 | Kalloo et al. | |
| 2002/0055757 A1 | 5/2002 | Torre et al. | |
| 2002/0072761 A1 | 6/2002 | Abrams et al. | |
| 2002/0082621 A1 | 6/2002 | Shurr et al. | |
| 2002/0099439 A1 | 7/2002 | Schwartz et al. | |
| 2002/0128677 A1 * | 9/2002 | Duerig | A61B 17/3207 606/198 |
| 2002/0183767 A1 | 12/2002 | Adams et al. | |
| 2002/0183768 A1 | 12/2002 | Deem et al. | |
| 2003/0009236 A1 | 1/2003 | Godin | |
| 2003/0040804 A1 | 2/2003 | Stack et al. | |
| 2003/0040808 A1 | 2/2003 | Stack et al. | |
| 2003/0065359 A1 | 4/2003 | Weller et al. | |
| 2003/0093117 A1 | 5/2003 | Saadat et al. | |
| 2003/0109892 A1 | 6/2003 | Deem et al. | |
| 2003/0109931 A1 | 6/2003 | Geitz | |
| 2003/0120289 A1 | 6/2003 | McGuckin, Jr. et al. | |
| 2003/0158569 A1 | 8/2003 | Wazne | |
| 2003/0191476 A1 | 10/2003 | Smit | |
| 2003/0191525 A1 | 10/2003 | Thornton | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2003/0208209 A1 | 11/2003 | Gambale et al. | |
| 2003/0220660 A1 | 11/2003 | Kortenbach et al. | |
| 2003/0236520 A1 * | 12/2003 | Lim | A61B 17/025 606/99 |
| 2004/0006351 A1 | 1/2004 | Gannoe et al. | |
| 2004/0024386 A1 | 2/2004 | Deem et al. | |
| 2004/0030347 A1 | 2/2004 | Gannoe et al. | |
| 2004/0044353 A1 | 3/2004 | Gannoe | |
| 2004/0044354 A1 | 3/2004 | Gannoe et al. | |
| 2004/0044357 A1 | 3/2004 | Gannoe et al. | |
| 2004/0044364 A1 | 3/2004 | DeVries et al. | |
| 2004/0059289 A1 | 3/2004 | Garza et al. | |
| 2004/0068276 A1 | 4/2004 | Golden et al. | |
| 2004/0082963 A1 | 4/2004 | Gannoe et al. | |
| 2004/0088023 A1 | 5/2004 | Imran et al. | |
| 2004/0092892 A1 | 5/2004 | Kagan et al. | |
| 2004/0092974 A1 | 5/2004 | Gannoe et al. | |
| 2004/0093091 A1 | 5/2004 | Gannoe et al. | |
| 2004/0098043 A1 | 5/2004 | Trout | |
| 2004/0107004 A1 | 6/2004 | Levine et al. | |
| 2004/0117031 A1 | 6/2004 | Stack et al. | |
| 2004/0138761 A1 | 7/2004 | Stack et al. | |
| 2004/0143342 A1 | 7/2004 | Stack et al. | |
| 2004/0148034 A1 | 7/2004 | Kagan et al. | |
| 2004/0153167 A1 | 8/2004 | Stack et al. | |
| 2004/0158331 A1 | 8/2004 | Stack et al. | |
| 2004/0162568 A1 | 8/2004 | Saadat et al. | |
| 2004/0172141 A1 | 9/2004 | Stack et al. | |
| 2004/0172142 A1 | 9/2004 | Stack et al. | |
| 2004/0186502 A1 | 9/2004 | Sampson et al. | |
| 2004/0210243 A1 | 10/2004 | Gannoe et al. | |
| 2004/0215216 A1 | 10/2004 | Gannoe et al. | |
| 2004/0220682 A1 | 11/2004 | Levine et al. | |
| 2004/0225183 A1 | 11/2004 | Michlitsch et al. | |
| 2004/0225305 A1 | 11/2004 | Ewers et al. | |
| 2004/0236419 A1 | 11/2004 | Milo | |
| 2004/0243152 A1 | 12/2004 | Taylor et al. | |
| 2004/0243223 A1 | 12/2004 | Kraemer et al. | |
| 2004/0254636 A1 | 12/2004 | Flagle et al. | |
| 2004/0267378 A1 | 12/2004 | Gazi et al. | |
| 2005/0004430 A1 | 1/2005 | Lee et al. | |
| 2005/0004681 A1 | 1/2005 | Stack et al. | |
| 2005/0033326 A1 | 2/2005 | Briganti et al. | |
| 2005/0033345 A1 | 2/2005 | DeLegge | |
| 2005/0049718 A1 | 3/2005 | Dann et al. | |
| 2005/0075654 A1 | 4/2005 | Kelleher | |
| 2005/0080444 A1 | 4/2005 | Kraemer et al. | |
| 2005/0085787 A1 | 4/2005 | Laufer et al. | |
| 2005/0096673 A1 | 5/2005 | Stack et al. | |
| 2005/0096750 A1 | 5/2005 | Kagan et al. | |
| 2005/0119671 A1 | 6/2005 | Reydel et al. | |
| 2005/0125020 A1 | 6/2005 | Meade et al. | |
| 2005/0125075 A1 * | 6/2005 | Meade | A61B 17/0401 623/23.64 |
| 2005/0149114 A1 | 7/2005 | Cartledge et al. | |
| 2005/0159769 A1 | 7/2005 | Alverdy | |
| 2005/0177181 A1 | 8/2005 | Kagan et al. | |
| 2005/0182416 A1 * | 8/2005 | Lim | A61B 17/025 606/90 |
| 2005/0183732 A1 | 8/2005 | Edwards | |
| 2005/0192599 A1 | 9/2005 | Demarais | |
| 2005/0192615 A1 | 9/2005 | Torre et al. | |
| 2005/0192629 A1 | 9/2005 | Saadat et al. | |
| 2005/0197714 A1 | 9/2005 | Sayet | |
| 2005/0216040 A1 | 9/2005 | Gertner et al. | |
| 2005/0216042 A1 | 9/2005 | Gertner | |
| 2005/0228504 A1 | 10/2005 | Demarais et al. | |
| 2005/0240279 A1 | 10/2005 | Kagan et al. | |
| 2005/0245965 A1 | 11/2005 | Orban et al. | |
| 2005/0247320 A1 | 11/2005 | Stack et al. | |
| 2005/0250980 A1 | 11/2005 | Swanstrom et al. | |
| 2005/0251158 A1 | 11/2005 | Saadat et al. | |
| 2005/0251162 A1 | 11/2005 | Rothe et al. | |
| 2005/0256533 A1 | 11/2005 | Roth et al. | |
| 2005/0256587 A1 | 11/2005 | Egan | |
| 2005/0261712 A1 | 11/2005 | Balbierz et al. | |
| 2005/0267405 A1 | 12/2005 | Shah | |
| 2005/0267499 A1 | 12/2005 | Stack et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |

(56) References Cited

U.S. PATENT DOCUMENTS

| | | |
|---|---|---|
| 2006/0004455 A1* | 1/2006 | Leonard ............... A61F 2/44 623/17.15 |
| 2006/0020278 A1 | 1/2006 | Burnette et al. |
| 2006/0058829 A1 | 3/2006 | Sampson et al. |
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0235423 A1* | 10/2006 | Cantu ............... A61B 17/8858 606/90 |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0027548 A1 | 2/2007 | Levine et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0116244 A1 | 5/2008 | Rethy et al. |
| 2008/0183203 A1* | 7/2008 | Fitzgerald ........ A61B 17/12022 606/194 |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0234703 A1 | 9/2008 | Cropper et al. |
| 2008/0269797 A1 | 10/2008 | Stack et al. |
| 2008/0294179 A1 | 11/2008 | Balbierz et al. |
| 2008/0319471 A1 | 12/2008 | Sosnowski et al. |
| 2009/0018558 A1 | 1/2009 | Laufer et al. |
| 2009/0024143 A1 | 1/2009 | Crews et al. |
| 2009/0030284 A1 | 1/2009 | Cole et al. |
| 2009/0093839 A1 | 4/2009 | Kelleher |
| 2009/0125040 A1 | 5/2009 | Hambley et al. |
| 2009/0171383 A1 | 7/2009 | Cole et al. |
| 2009/0177215 A1 | 7/2009 | Stack et al. |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0299487 A1 | 12/2009 | Stack et al. |
| 2010/0016988 A1 | 1/2010 | Stack et al. |
| 2010/0069819 A1 | 3/2010 | Laufer |
| 2010/0100109 A1 | 4/2010 | Stack et al. |
| 2010/0116867 A1 | 5/2010 | Balbierz et al. |
| 2010/0204719 A1 | 8/2010 | Balbierz et al. |
| 2011/0004146 A1 | 1/2011 | Priplata et al. |
| 2011/0046537 A1 | 2/2011 | Errico et al. |
| 2011/0153030 A1 | 6/2011 | Stack et al. |
| 2011/0295179 A1 | 12/2011 | Harris et al. |
| 2011/0295180 A1 | 12/2011 | Albrecht et al. |
| 2012/0296254 A1 | 11/2012 | Swain et al. |
| 2012/0310138 A1 | 12/2012 | Behan |
| 2013/0079603 A1 | 3/2013 | Vargas |
| 2013/0267886 A1 | 10/2013 | Priplata et al. |
| 2014/0031738 A1 | 1/2014 | Errico et al. |
| 2016/0022464 A1* | 1/2016 | Stack ............... A61F 5/0089 623/23.65 |

FOREIGN PATENT DOCUMENTS

| | | |
|---|---|---|
| EP | 0775471 | 5/1997 |
| EP | 1256318 A1 | 11/2002 |
| EP | 1492478 | 1/2005 |
| EP | 1602336 | 12/2005 |
| FR | 2768324 | 3/1999 |
| JP | 09-168597 | 6/1997 |
| WO | WO 91/01117 | 2/1991 |
| WO | WO 95/25468 A1 | 9/1995 |
| WO | WO 97/47231 | 12/1997 |
| WO | WO 00/12027 | 3/2000 |
| WO | WO 00/32137 | 6/2000 |
| WO | WO 00/78227 | 12/2000 |
| WO | WO 01/41671 | 6/2001 |
| WO | WO 01/45485 | 6/2001 |
| WO | WO 01/49359 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 | 11/2003 |
| WO | WO 03/094785 | 11/2003 |
| WO | WO 03/099137 | 12/2003 |
| WO | WO 03/105698 A2 | 12/2003 |
| WO | WO 2004/019765 | 3/2004 |
| WO | WO 2004/019787 | 3/2004 |
| WO | WO 2004/032760 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 | 12/2004 |
| WO | WO 2005/037152 | 4/2005 |
| WO | WO 2005/079673 | 9/2005 |
| WO | WO 2005/096991 | 10/2005 |
| WO | WO 2005/105003 | 11/2005 |
| WO | WO 2006/016894 | 2/2006 |
| WO | WO 2006/055365 | 5/2006 |
| WO | WO 2006/127593 | 11/2006 |
| WO | WO 2007/041598 | 4/2007 |
| WO | WO 2008/030403 | 3/2008 |
| WO | WO 2008/033409 | 3/2008 |
| WO | WO 2008/033474 | 3/2008 |
| WO | WO 2008/141288 | 11/2008 |
| WO | WO 2009/011881 | 1/2009 |
| WO | WO 2009/011882 | 1/2009 |
| WO | WO 2009/086549 | 7/2009 |
| WO | WO 2009/117533 | 9/2009 |
| WO | WO 2010/054399 | 5/2010 |
| WO | WO 2010/054404 | 5/2010 |

OTHER PUBLICATIONS

International Search Report from PCT Patent Application No. PCT/US2002/027177 dated Feb. 14, 2003.
International Search Report from PCT Patent Application No. PCT/US2003/004378 dated Aug. 13, 2003.
International Search Report from PCT Patent Application No. PCTIUS2003/033605 dated Mar. 29, 2004.
International Search Report from PCT Patent Application No. PCT/US2003/033606 dated Mar. 29, 2004.
International Search Report from PCT Patent Application No. PCT/US2003/004449 dated Aug. 13, 2003.
International Search Report from PCT Patent Application No. PCTIUS2004/006695 dated Sep. 8, 2004.

(56) References Cited

OTHER PUBLICATIONS

International Search Report from PCT Patent Application No. PCTIUS2004/033007 dated Feb. 9, 2005.
International Search Report from PCT Patent Application No. PCTIUS2005/014372 dated Jul. 28, 2005 294.
International Search Report from PCT Patent Application No. PCT/US2006/019727 dated Apr. 19, 2007.
International Search Report from PCT Patent Application No. PCT/US2006/038684 dated Feb. 14, 2007.
International Search Report from PCT Patent Application No. PCTIUS2007/019227 dated Feb. 20, 2008.
International Search Report from PCT Patent Application No. PCTIUS2007/019833 dated Feb. 20, 2008.
International Search Report from PCT Patent Application No. PCTIUS2007/019940 dated Mar. 14, 2008.
International Search Report from PCT Patent Application No. PCTIUS2008/008726 dated Oct. 16, 2008.
International Search Report from PCT Patent Application No. PCT/US2008/008729 dated Aug. 18, 2009.
International Search Report from PCT Patent Application No. PCT/US2008/063440 dated Aug. 1, 2008.
International Search Report from PCT Patent Application No. PCTIUS2008/088581 dated Feb. 26, 2009.
International Search Report from PCT Patent Application No. PCT/US2009/037586 dated Sep. 28, 2009.
International Search Report from PCT Patent Application No. PCT/US2009/063925 dated Jan. 12, 2010.
International Search Report from PCT Patent Application No. PCT/US2009/063930 dated Jan. 12, 2010.
Felsher et al., "Mucosal apposition in endoscopic suturing", Gastrointestinal Endoscopy, vol. 58, No. 6, pp. 867-870, (2003).
Stecco et al., "Trans-oral plication formation and gastric implant placement in a canine model", Stecco Group, San Jose and Barosense, Inc., Redwood City, CA (2004).
Stecco et al. "Safety of a gastric restrictive implant in a canine model", Stecco group, San Jose amd Barosense, Inc., Redwood City, CA (2004).

\* cited by examiner

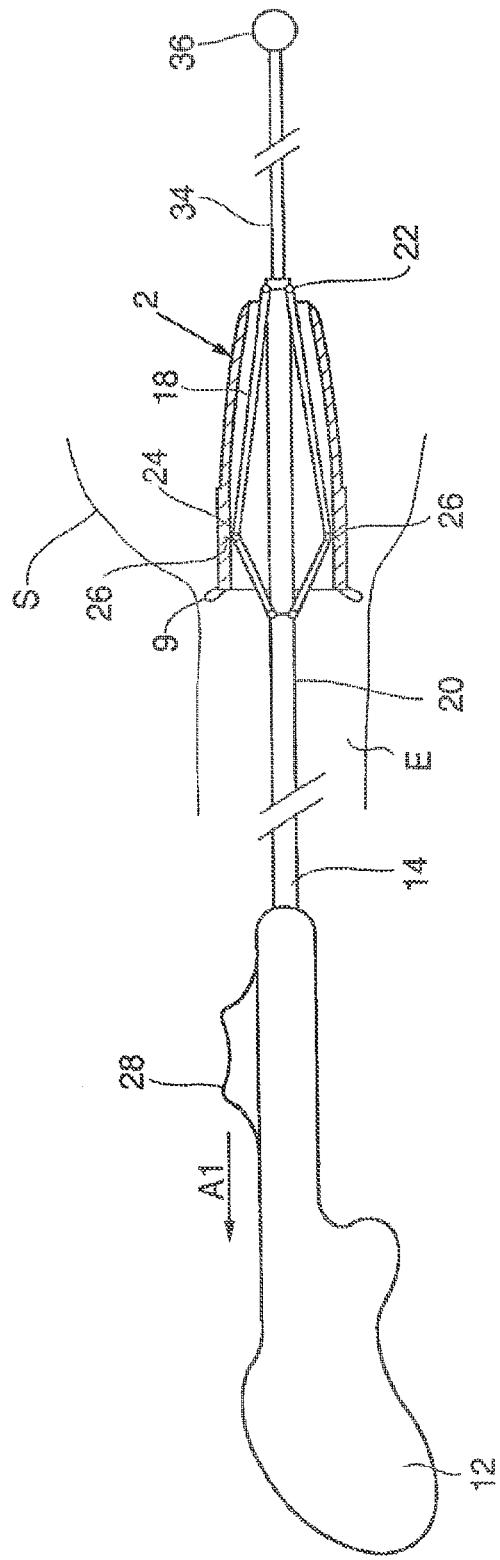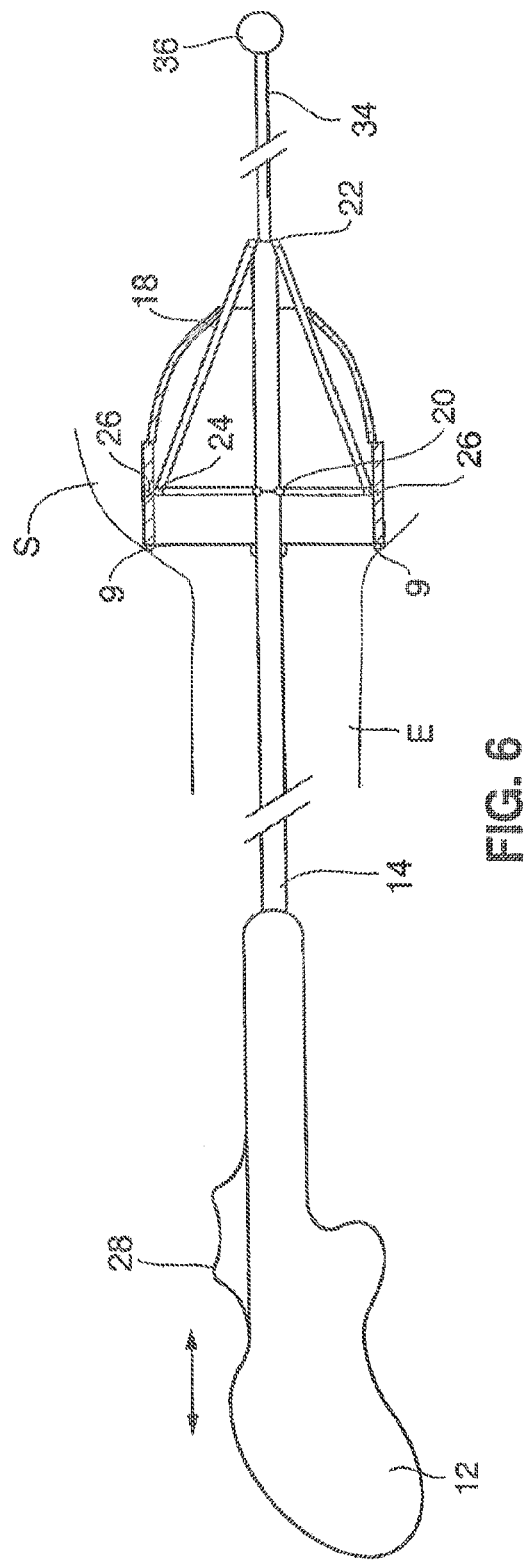

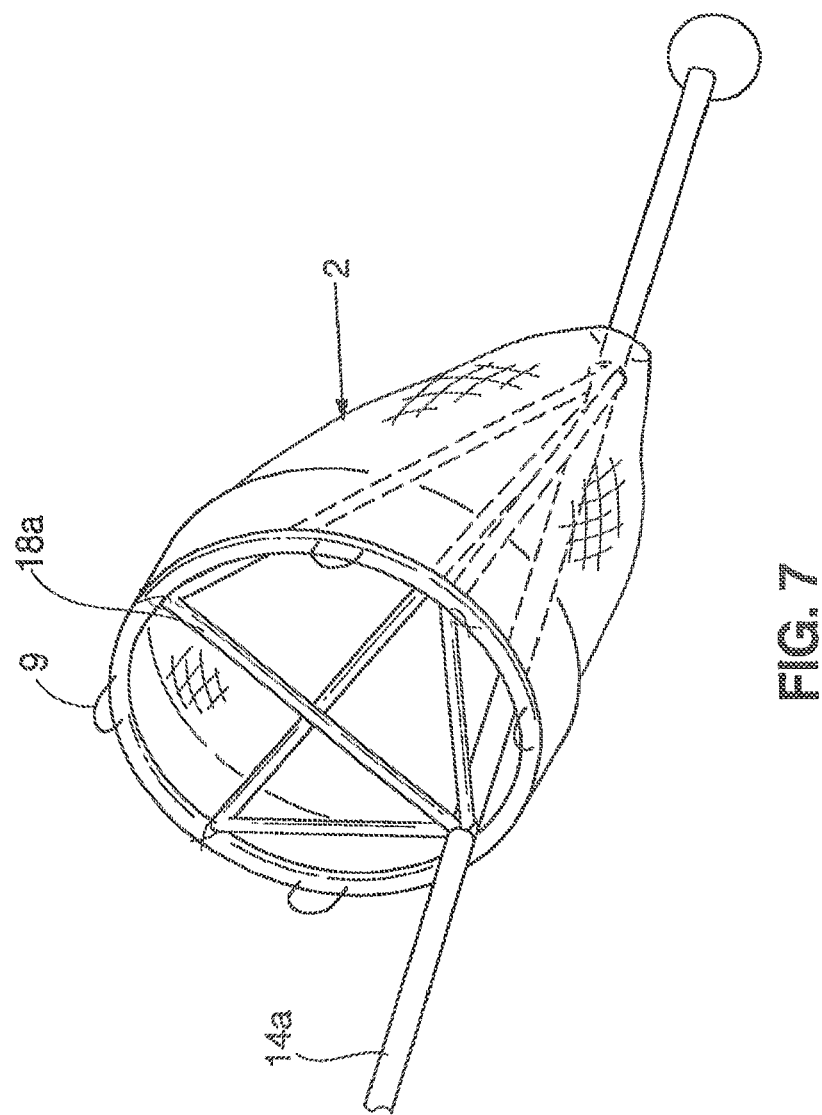

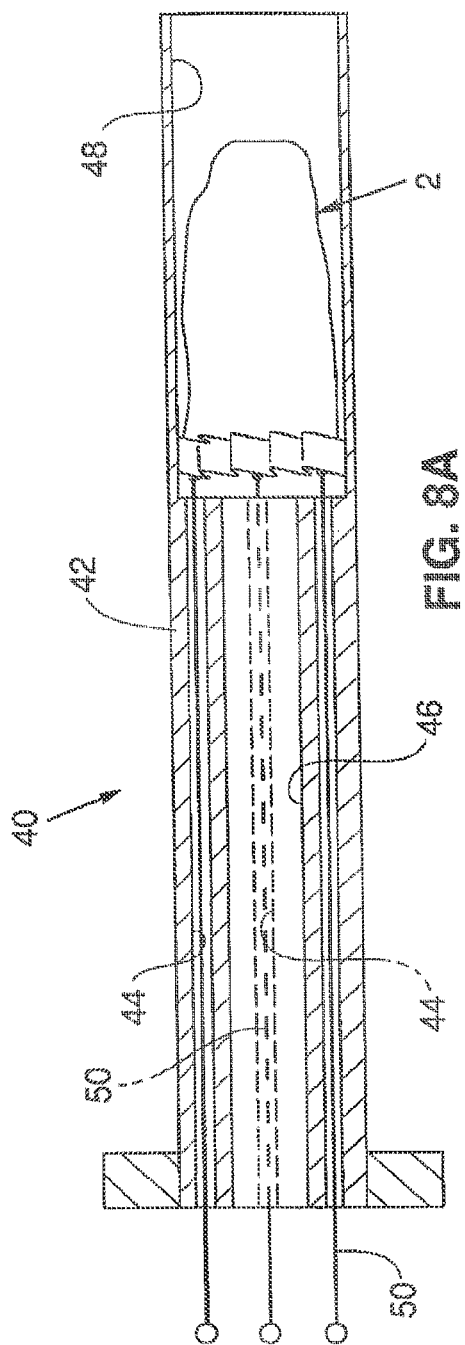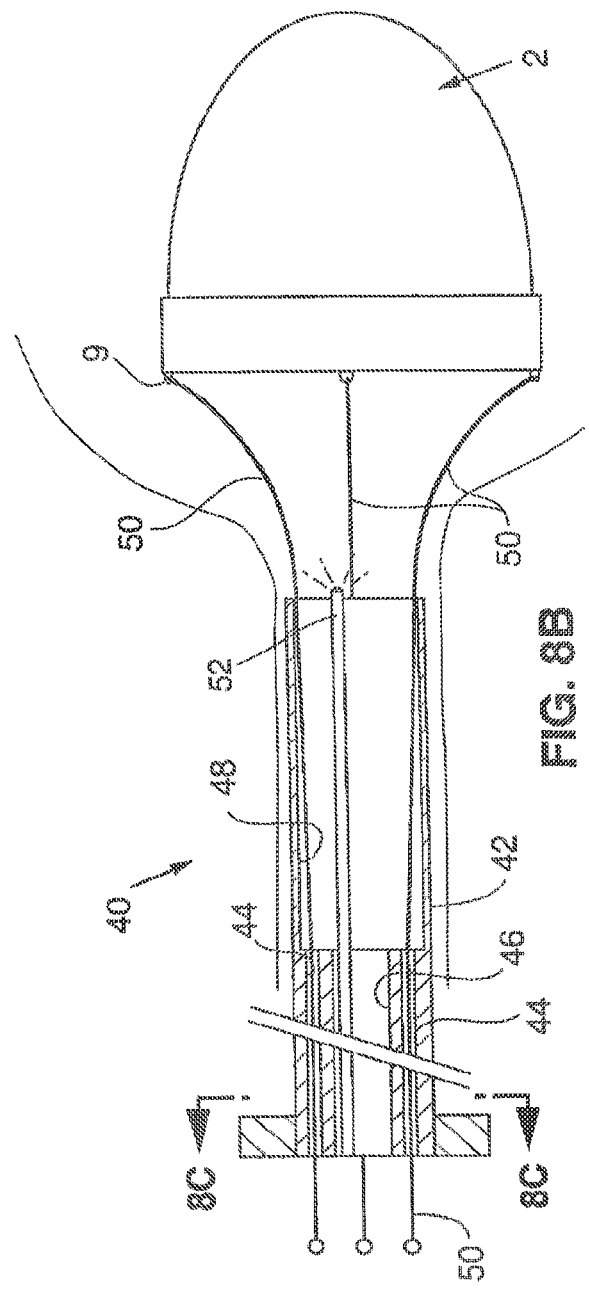

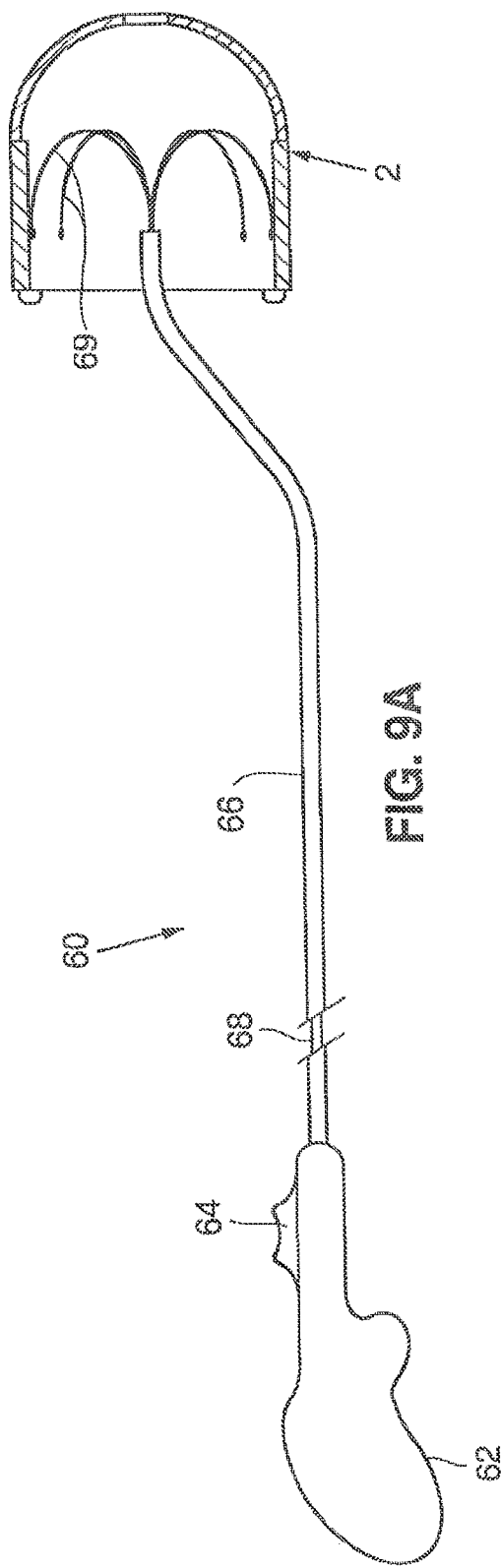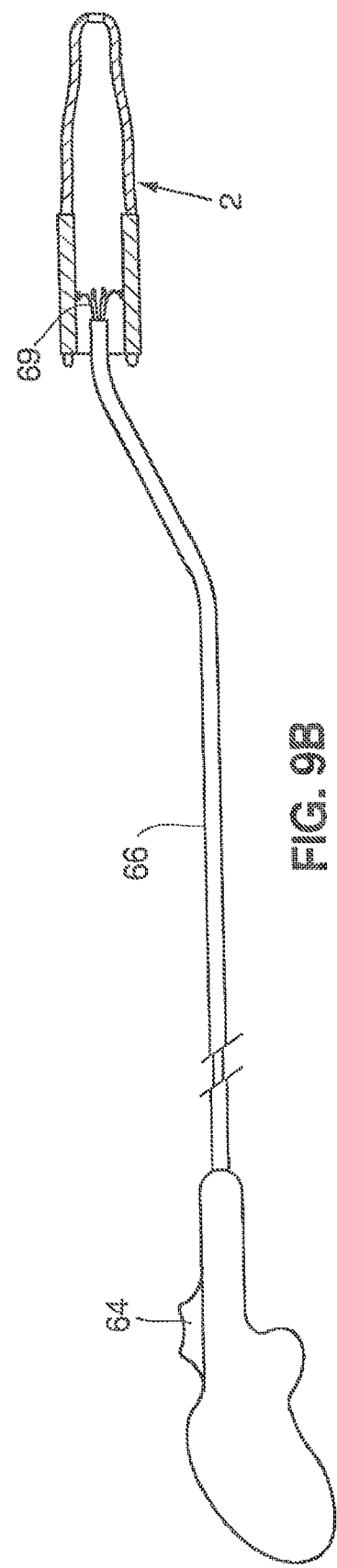

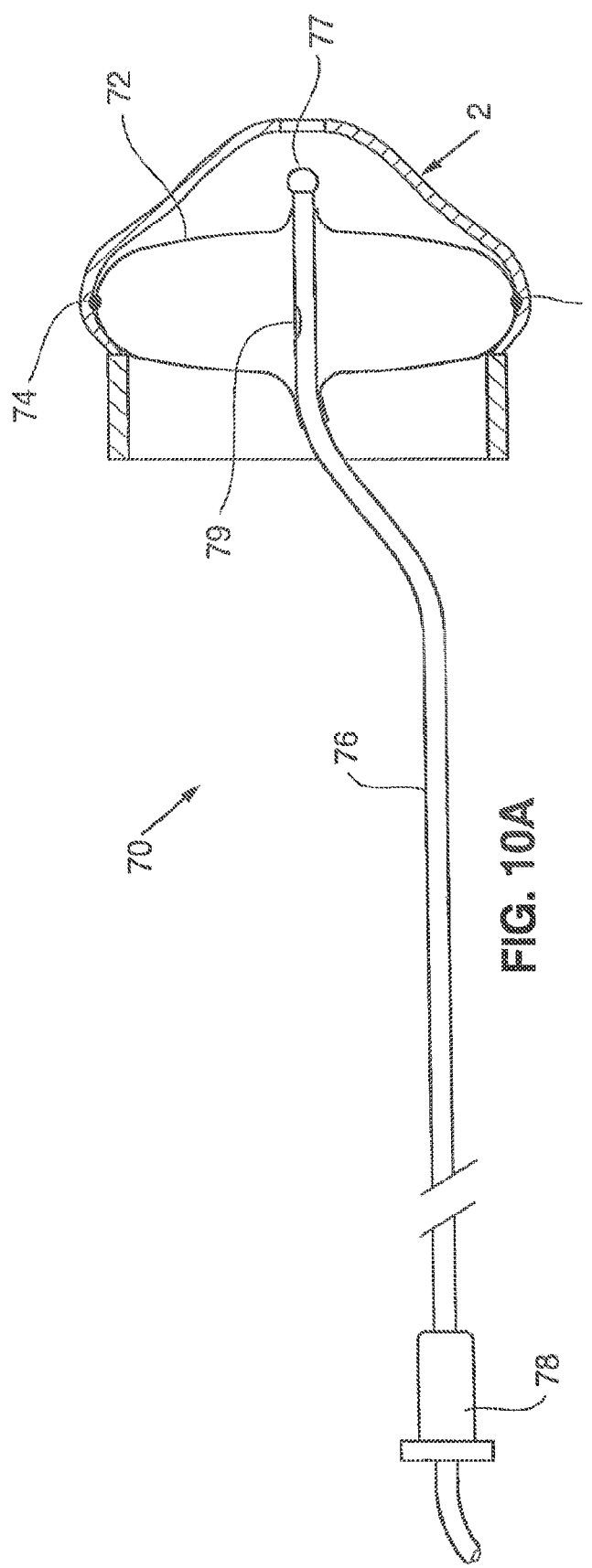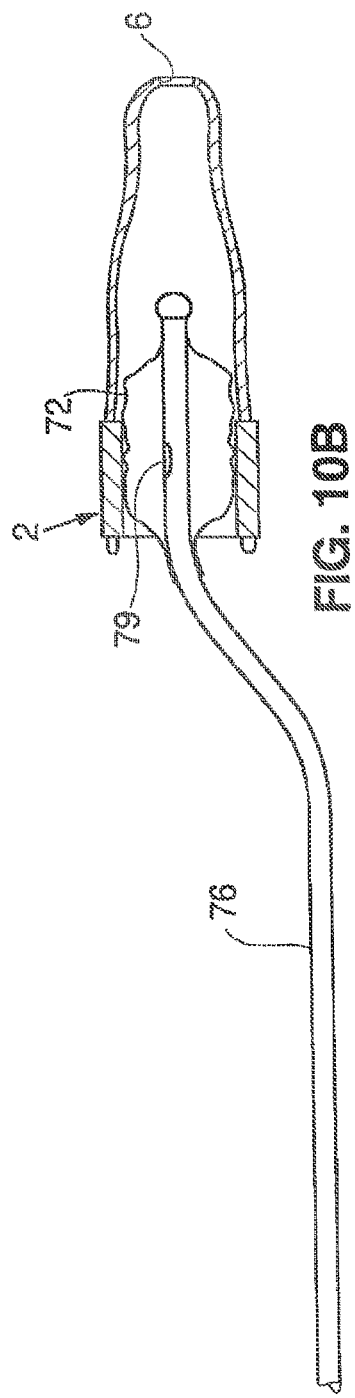

POSITIONING TOOLS AND METHODS FOR IMPLANTING MEDICAL DEVICES

This application is a continuation of U.S. patent application Ser. No. 14/305,255, filed Jun. 16, 2014, which is a continuation of U.S. patent application Ser. No. 13/032,569, filed Feb. 22, 2011, now U.S. Pat. No. 8,784,354, which is a continuation of U.S. patent application Ser. No. 11/479,204, filed Jun. 30, 2006, now U.S. Pat. No. 7,892,292, which is a divisional of U.S. patent application Ser. No. 10/345,698, filed Jan. 16, 2003, now U.S. Pat. No. 7,097,665, and is a continuation-in-part of U.S. patent application Ser. No. 10/751,751, filed Jan. 5, 2004, now U.S. Pat. No. 7,981,162, which is a divisional of U.S. patent application Ser. No. 10/118,289, filed Apr. 8, 2002, now U.S. Pat. No. 6,845,776, which is a continuation-in-part of U.S. patent application Ser. No. 09/940,110, filed Aug. 27, 2001, now U.S. Pat. No. 6,675,809.

FIELD OF THE INVENTION

The present invention relates generally to the field of tools and methods for facilitating implantation of medical devices, and specifically to tools and methods for expanding and positioning medical implants into the proper position for attachment to body tissue.

BACKGROUND OF THE INVENTION

In various types of surgical procedures, medical devices are implanted at locations within the human body that are neither susceptible to direct visualization by the surgeon nor accessible by the surgeon's fingers. Such procedures are therefore performed using endoscopes for visualization and endoscopic instruments for carrying out the procedures. Once such procedure is the implantation of satiation devices used to limit volume of food intake and/or control feeling of hunger in patients suffering from obesity. In a preferred approach, such devices are passed through the esophagus into the stomach and are then secured within the stomach using sutures, clips, staples, adhesives etc. The tools and methods described herein are useful for introducing satiation devices into the stomach and for manipulating the devices into the appropriate implant position, and will thus will be described in that context. It should be understood, however, that these tools and methods may also be well suited for use with other types of medical implants and/or in other areas of the body.

An anatomical view of a human stomach S and associated features is shown in FIG. 1. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the zline, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Implant devices for use in controlling obesity are shown and described in U.S. application Ser. No. 09/940,110, filed Aug. 27, 2001 and U.S. application Ser. No. 10/118,289 filed Apr. 8, 2002, U.S. Provisional Application No. 60/379,306 filed May 10, 2002, and U.S. application Ser. No. 10/345,914, filed Jan. 16, 2003 entitled SATIATION POUCHES AND METHODS OF USE. These applications are owned by the assignee of the present application, and the disclosures of these applications are incorporated herein by reference. One type of satiation device described in these applications is a prosthetic pouch positionable in the proximal stomach as shown in FIG. 2. The pouch 2 includes a proximal opening 4 and a smaller distal opening 6 and forms a small reservoir that collects masticated food from the esophagus—thereby limiting the amount of food that can be consumed at one time. As the pouch fills with food, it may distend, imparting pressure against the upper stomach and lower esophageal sphincter causing the patient to experience sensations of fullness. The pouch is fixed in place using clips, sutures or similar means 8 at anchor points around the perimeter of the proximal opening 4. Wire anchor loops 9 are preferably provided for receiving sutures or clips, although the pouch could also be secured to tissue using sutures, staples, clips, etc passed directly through the pouch walls. Alternatively, windows 7 may be formed in the pouch for receiving sutures during attachment of the pouch to adjacent tissue.

Optimal performance of the pouch is achieved when substantially all of the food ingested by the patient passes into the pouch. However, because of the flexible nature of the tissue of the gastro-esophageal junction region and/or the material forming the pouch, gaps can occur between the proximal perimeter of the pouch and adjacent tissue in regions between neighboring anchor points. Food entering or accumulating in the pouch can ooze from these gaps and pass around the exterior of the pouch directly into the stomach, thereby decreasing the effectiveness of the prosthesis. It is thus desirable to attach the pouch in a position and at an orientation that minimizes formation of gaps between anchor points.

SUMMARY OF THE INVENTION

Described herein is a positioning tool having an elongate portion for carrying a medical implant. Also described is a method of positioning a medical implant using an elongate positioning tool. One form of the method includes positioning a medical implant on a distal portion of an elongate positioning tool, inserting the positioning tool with the implant thereon into a body cavity, manipulating the positioning tool to position the implant into contact with tissue at an attachment location, attaching the implant to surrounding tissue at the attachment location, separating the implant from the positioning tool, and withdrawing the positioning tool from the body. In a preferred embodiment, the position of the implant is visually confirmed using an endoscope before the implant is attached to surrounding tissue. In one embodiment, the implant is a satiation device and the body cavity is the esophagus and/or stomach. In an alternative embodiment, an expansion structure on the distal end of the elongate portion expands and/or contracts the medical implant to facilitate positioning.

BRIEF DESCRIPTION OF THE DRAWINGS

FIG. 5 is a side elevation view of the positioning tool of FIG. 3, schematically illustrating insertion of the tool and pouch through the esophagus and into the stomach. The pouch is shown in cross-section.

FIG. 6 is a side elevation view similar to FIG. 5, but showing the tool expanding the pouch and positioning the pouch at the attachment site. The pouch is shown in cross-section.

FIG. 7 is a perspective view similar to FIG. 4 showing a slightly modified configuration in which the cannula is laterally offset from the central axis of the pouch.

FIG. 8A is a side elevation view showing a second embodiment of a positioning tool and a pouch in the collapsed position.

FIG. 8B is a side elevation view similar to FIG. 8A showing the second embodiment and pouch in the expanded position.

FIGS. 9A and 9B are side elevation views showing a third embodiment of a positioning tool supporting a pouch in the expanded and collapsed positions, respectively.

FIGS. 10A and 10B are side elevation views showing a fourth embodiment of a positioning tool supporting a pouch in the expanded and collapsed positions, respectively.

DETAILED DESCRIPTION OF THE DRAWINGS

Figure 1:
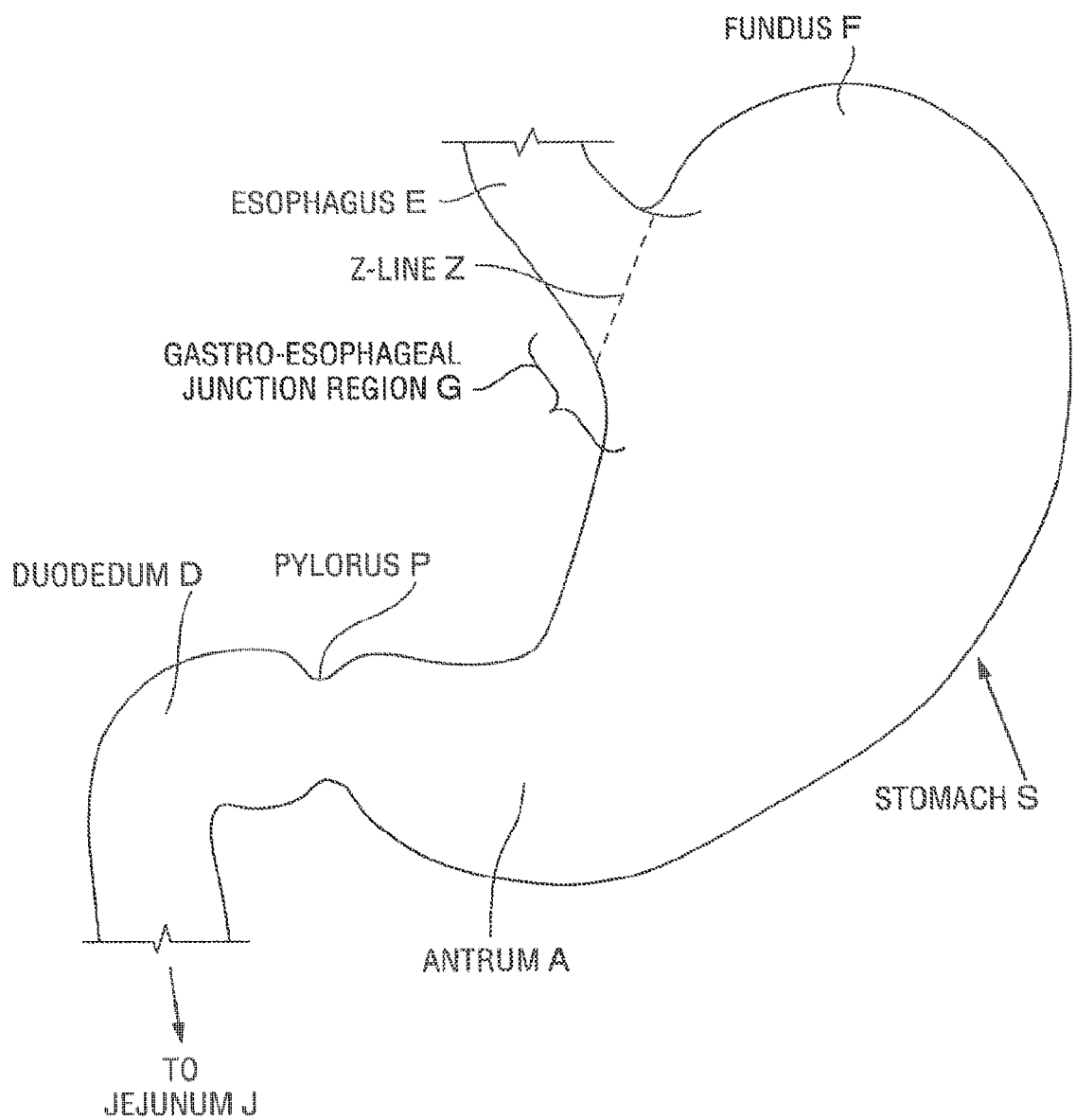
FIG. 1 is a schematic illustration of a human stomach and a portion of the small intestine.

The positioning tools and methods of use will be described in connection with implantation of satiation pouches such as pouch 2 of FIG. 1. Descriptions of various embodiments of pouches and other satiation devices are found in U.S. application Ser. No. 09/940,110, filed Aug. 27, 2001 and U.S. application Ser. No. 10/118,289 filed Apr. 8, 2002, U.S. Provisional Application No. 60/379,306 filed May 10, 2002, and U.S. application Ser. No. 10/345,914, filed Jan. 16, 2003 entitled SATIATION POUCHES AND METHODS OF USE, each of which is incorporated herein by reference.

For the purposes of this application, the term "satiation devices" will be used to mean devices intended to induce weight loss in one or more of a variety of ways. These include, but are not limited to, physically restricting the amount of food that can be consumed, and/or imparting pressure against portions of the body (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body.

Such pouches may be formed of a flexible material that will prevent passage of food through the sides of the pouch. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The material may be a composite of compliant, semi-compliant and/or non-compliant materials that give different regions of the pouch different degrees of compliance so as to allow/limit expansion of the pouch in various locations. For example, it may be desirable to provide the pouch with a fairly elastic exit port to as to prevent occlusion in the event a large piece of food is ingested and/or to control the exit pressure of food from the pouch, whereas the proximal end of the pouch may be stiffer to prevent bulging. Varying degrees of compliance may also be built into the pouch by varying the cross-sectional thickness in different regions of the pouch. The material may be coated with a lubricious, bio-compatible, chemically inert material, such as paraleyne, to reduce friction on the base material's surface which will help prevent sticking and food build up on the device.

The flexible pouch material may be reinforced with, constructed of, or supported by supporting members, such as a soft mesh, a cage structure, ribs, rings etc. The supporting members may be formed of stainless steel, polymer, shape memory materials such as nitinol, shape memory alloys, or shape memory polymers, or thickened regions of material. The pouch may be constructed so as to be self-expanding, such that the pouch springs radially open into an expanded condition upon ejection from a deployment device or catheter.

Implantation of the satiation devices is preferably performed endoscopically, by passing the devices through the esophagus, preferably under endoscopic visualization. Alternatively, the devices may be implanted using surgical or laparoscopic procedures.

Figure 2:
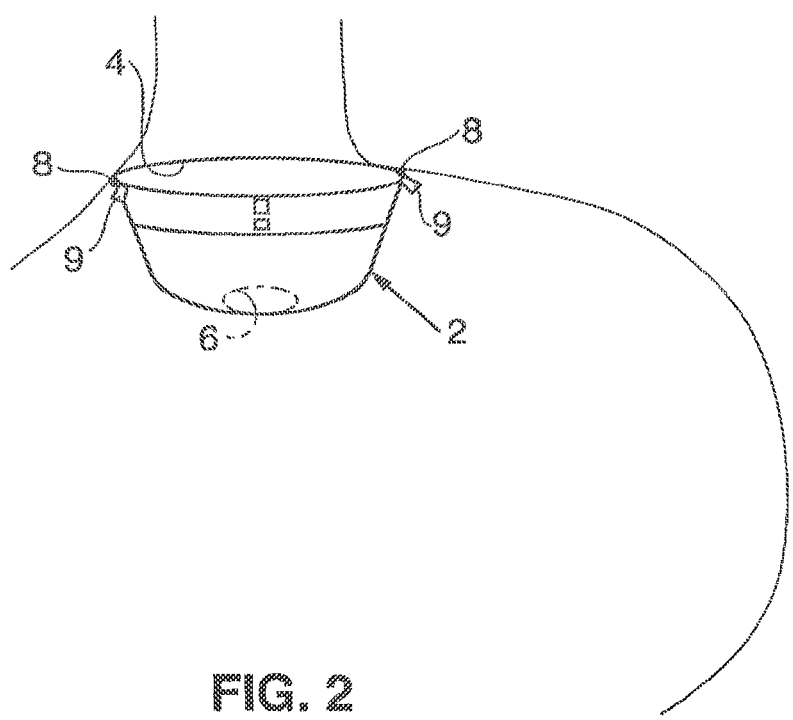
FIG. 2 is a perspective view of at satiation pouch of a type that may be positioned using the tools of FIGS. 3 through 11. The pouch is shown positioned in the stomach.

Pouches of this type include a proximal opening and a smaller diameter distal exit port (see openings 4 and 6, respectively, of FIG. 2). Because of its small volume (which may be on the order of approximately 2 cc-300 cc in volume, but is preferably in the range of 10-30 cc), the pouch functions to limit the amount of food that can be consumed at one time. Over time the food within this reservoir descends into the stomach through the exit port. During implantation, the pouch is secured at the gastro-esophageal junction region G using sutures, clips, adhesives, staples, stents, or other suitable means. Although the pouch may be secured to the esophageal tissue, it is more preferable to apply sutures/clips etc below the Zline to allow for attachment to the thicker tissue of the stomach wall. An endoscopic device for applying sutures between the device and tissue, such as the flexible "Sew-Right" device (not shown) available from LSI Solutions of Victor, N.Y., may be used to complete the attachment, although sutures, staples, clips or adhesives may be applied using alternative means.

First Embodiment

Figure 3:
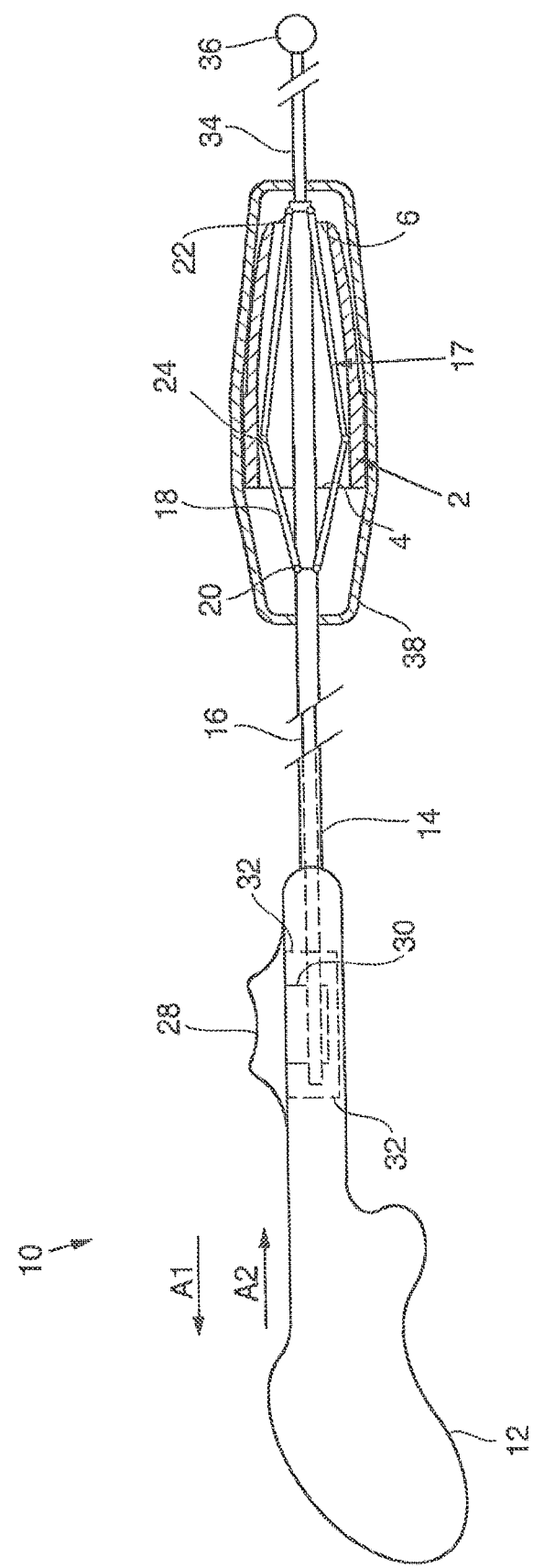
FIG. 3 is a side elevation view of a first embodiment of a positioning tool, shown supporting a pouch in a collapsed position. The pouch is shown in cross-section to permit the features of the tool to be seen.

FIG. 3 shows a first embodiment of a positioning tool. Tool 10 includes a handle 12 and a cannula 14 extending longitudinally from the distal end of the handle 12. An advancement mandrel 16 is slidably disposed within the cannula 14.

An expansion structure 17 is provided for supporting and expanding a pouch 2 for insertion into the stomach. Expansion structure 17 of the first embodiment is formed of a system of rods 18. Each rod includes a proximal end 20 pivotally connected to cannula 14, and a distal end 22 pivotally connected to mandrel 16. Each rod 18 further includes an intermediate pivot point 24 between the proximal and distal ends. Pouch 2 is temporarily secured to rods 18, preferably at pivot points 24 using sutures 26 (FIG. 4) or other detachable fasteners or self-releasing mechanisms.

A sliding member 28 is slidably positioned on handle 12. Sliding member 28 includes a lower portion 30 that is moveable within a corresponding slot 32 in the handle. Lower portion 30 is fixed to the mandrel 16 such that movement of the sliding member 28 in a proximal or distal direction produces corresponding movement of the mandrel 16.

Mandrel 16 may (optionally) be of sufficient length to extend through the distal opening 6 of pouch 2, forming a distal guide member 34 that provides tactile guidance to the physician during advancement of the mandrel into the esophagus and stomach. Guide member 34 is preferably flexible and includes an atraumatic tip 36 which minimizes tissue damage when the tip is advanced into contact to tissue of the esophagus or stomach. Examples of atraumatic tip configurations include, the spherical bead in FIG. 4 or a J-wire tip. Alternatively, mandrel 16 may be sized such that its distal end terminates within the pouch 2.

Prior to use, sliding member 28 is initially advanced in a distal direction as indicated by arrow A2 in FIG. 3. Distal movement of sliding member 28 causes mandrel 16 to push the distal ends 22 of rods 18 distally, causing the expansion structure 17 to collapse into the configuration shown in FIG. 3. Next, tip 36 of mandrel 16 is passed through the proximal and distal openings 4, 6, of the pouch 2, and the pouch is drawn onto the rods 18. The pouch is temporarily sutured to the rods, preferably at intermediate pivot points 24. A sheath 38 may be positioned over the pouch and rods to provide a more streamlined profile for insertion through the esophagus.

Referring to FIG. 5, the expansion structure 17 and pouch 2 are inserted into the patient's oral cavity, down the esophagus E, and into the stomach S. If used, the sheath 38 (not shown in FIG. 5) is removed from the pouch and withdrawn from the stomach using an endoscopic grasping device or other means such as a tether.

The sliding member 28 is withdrawn in the proximal direction A1, causing the mandrel 16 to pull the distal ends 22 of the rods 18 in the proximal direction, towards the proximal ends 20 of the rods. This action causes the rods to flare outwardly at pivot points 24 in a manner resembling the expansion of a "moly bolt." This expansion of the rods drives the pouch into its expanded configuration as shown in FIG. 6.

Under endoscopic visualization, the handle 12 is pulled in a proximal direction to draw the proximal rim of the pouch 2 into contact with tissue at the desired attachment location. Once it is visually confirmed that the pouch is properly positioned, the pouch is fixed to the surrounding tissue using sutures, clips, staples etc. secured through anchor loops 9 (FIG. 6) or directly through the walls of the pouch. Alternatively, the pouch may be manipulated into the attachment location prior to expansion, then expanded into contact with surrounding tissue, and then anchored in place. Ideally, the rim of the pouch will form a seal with the adjacent tissue, however it is sufficient in each of the described embodiments that there is sufficient contact to prevent a substantial amount of food from passing between the exterior of the pouch and adjacent tissue, without necessarily forming an impermeable seal.

Next, the temporary sutures 26 connecting the pouch 2 to the expansion structure 17 are clipped, and the expansion structure is withdrawn into the collapsed position by advancing the sliding member 28 distally. The tool is withdrawn from the stomach, leaving the pouch in place.

Figure 4:
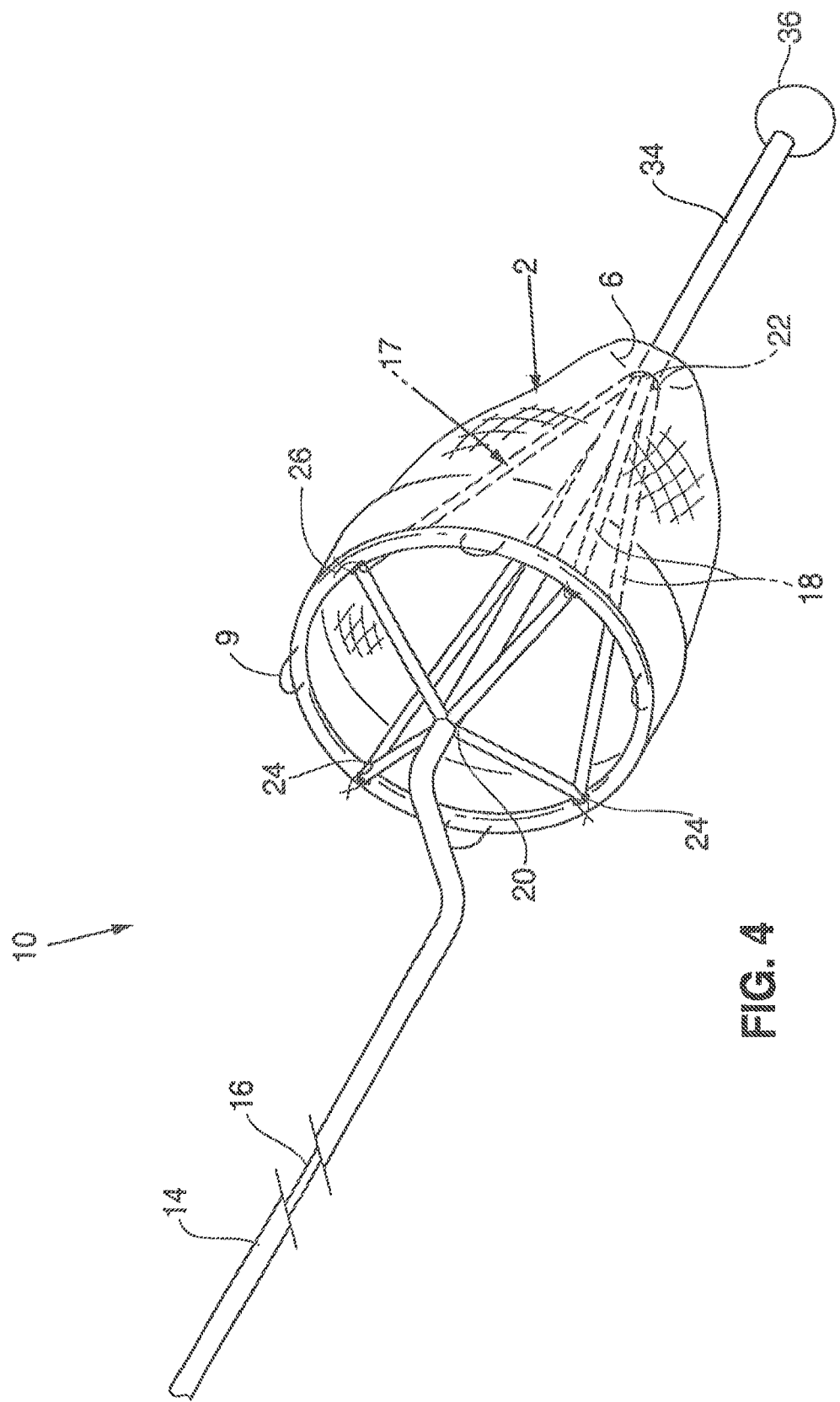
FIG. 4 is a perspective view of the distal portion of the positioning tool of FIG. 3, shown supporting a pouch (shown in phantom lines) in an expanded position.

It should be noted that cannula 14 may be substantially straight as shown in FIG. 3, or it may have the curved profile shown in FIG. 4. The curved configuration facilitates visualization of and access to the pouch, rods and sutures by allowing the handle to be laterally offset from the central axis of the pouch. If the curved cannula is used, the mandrel 16 should be sufficiently flexible to slide readily within the curved portion of the cannula.

In a slightly modified configuration shown in FIG. 7, the cannula 14a is offset from the central axis of the pouch 2 and three rods 18a function to expand the pouch.

Second Embodiment

Figure 8C:
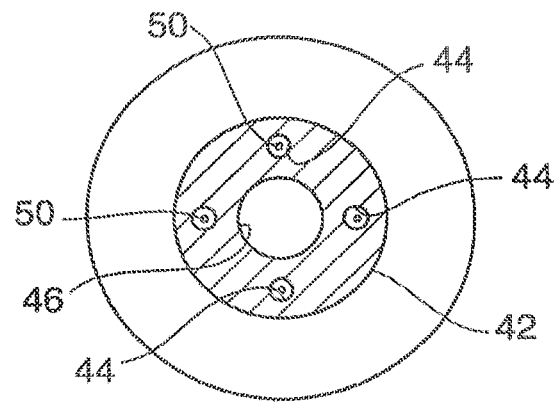
FIG. 8C is a cross-sectional end view of the second embodiment, taken along the plane designated 8C-8C in FIG. 8B.

FIGS. 8A and 8B show a second embodiment of a positioning tool 40. Tool 40 includes an elongate sheath 42 having a plurality of mandrel lumens 44 and a central lumen 46. The mandrel lumens 44 and central lumen 46 are continuous with a single, larger diameter distal lumen 48 positioned at the distal end of the sheath 42. Positioning mandrels 50 extend through mandrel lumens 44 and are temporarily attached to a pouch 2 at anchor loops 9 or at alternative locations, using sutures or other detachable or self-releasing means. Positioning mandrels may be spring biased in a radially outward position such that the mandrels spring outwardly when released from the sheath 42, to expand the pouch 2. On the other hand, the spring feature of the mandrels may be eliminated for a variety of reasons, for example if the pouch is constructed to be self-expanding, or if the mandrels may be simply steered to an outward orientation.

Prior to use, the pouch 2 and the distal ends of the mandrels 50 are disposed within the sheath 42, with the pouch 2 housed within the distal lumen 48 of the sheath. The sheath 42 is passed into the esophagus and advanced until the open distal end is disposed within the stomach. The proximal ends of the sheath 42 and mandrels 50 remain outside of the patient's oral cavity.

Positioning mandrels 50 are advanced to expel the pouch from the open end of the sheath 42 and to open the pouch to its expanded position as shown in FIG. 8B. An additional supporting mandrel or endoscopic grasper (not shown) may be extended through central lumen 46 and used to support the pouch during this and/or later stages of deployment.

An endoscope 52 is passed through the central lumen and advanced into the stomach and the sheath and mandrels are manipulated under endoscopic visualization to position the proximal portion of the pouch at the desired attachment location, such as at the gastro-esophageal junction region. For example, the sheath and/or the mandrels may be moved proximally or distally to adjust the proximal/distal location of the implant. The mandrels may be moved simultaneously or independently. The angle of the implant may be "fine tuned" to match the anatomy of the attachment location by individually adjusting the positioning mandrels.

Once the pouch is visually confirmed to be in an appropriate orientation for fixation, an attachment device is extended through the central lumen 46 and is used to apply sutures, staples, clips or adhesive to secure the pouch 2 to the surrounding tissue. Sutures connecting the positioning mandrels to the pouch are snipped and the mandrels are withdrawn. The endoscope and any remaining instruments are removed from the central lumen 46, and the sheath 42 is withdrawn from the patient, leaving the pouch positioned within the stomach. As is apparent from this description, the sheath 42 used in the second embodiment is advantageous in that it provides channels for the various tools employed, thereby protecting the esophagus from trauma and maintaining a working window by supporting the esophagus against collapse. It also allows clear access to anchor points on the implant since tools are passed through the central lumen of the sheath. If the sheath has a diameter that is large enough to minimize lateral play of the sheath within the esophagus, the sheath will also facilitate centering of the pouch and tools within the operative area.

Figure 8D:
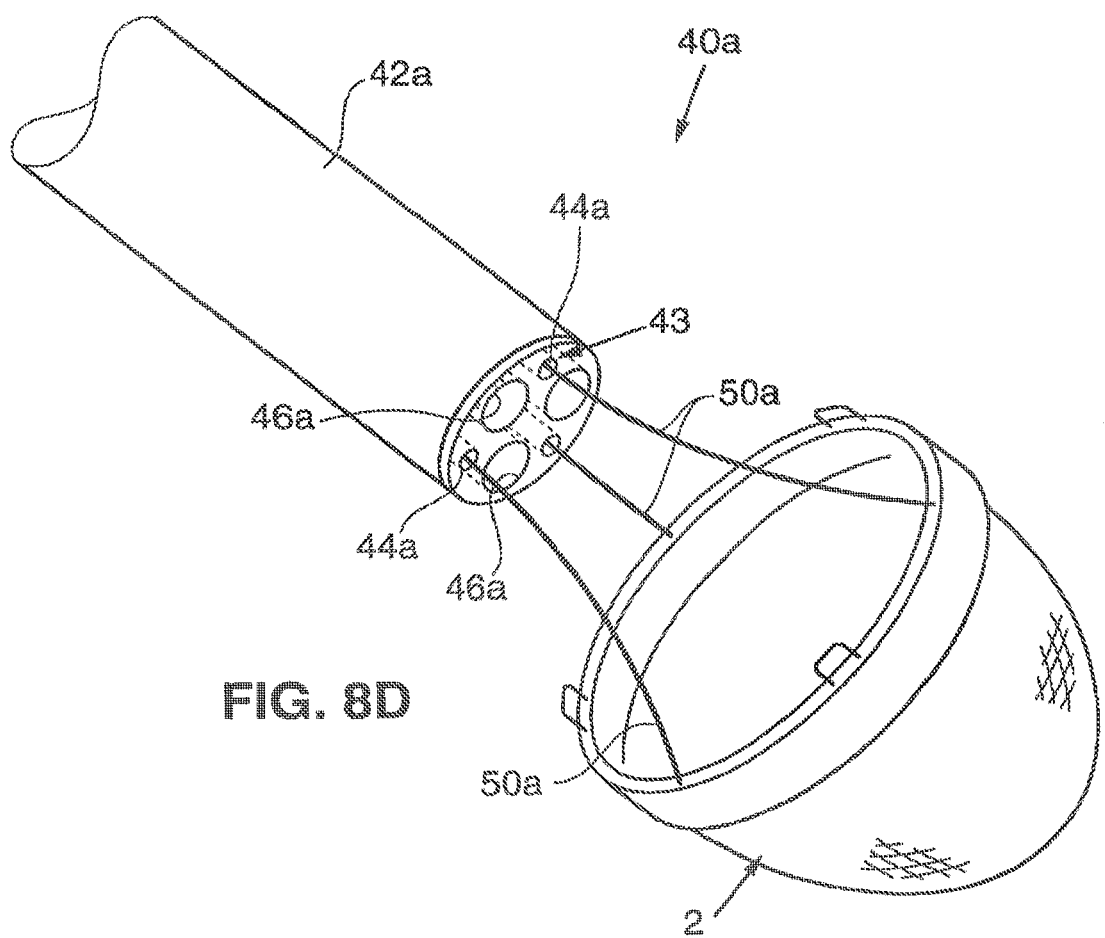
FIG. 8D is a perspective view of the distal portion of a variation of the embodiment of FIG. 8A.
Figure 8E:
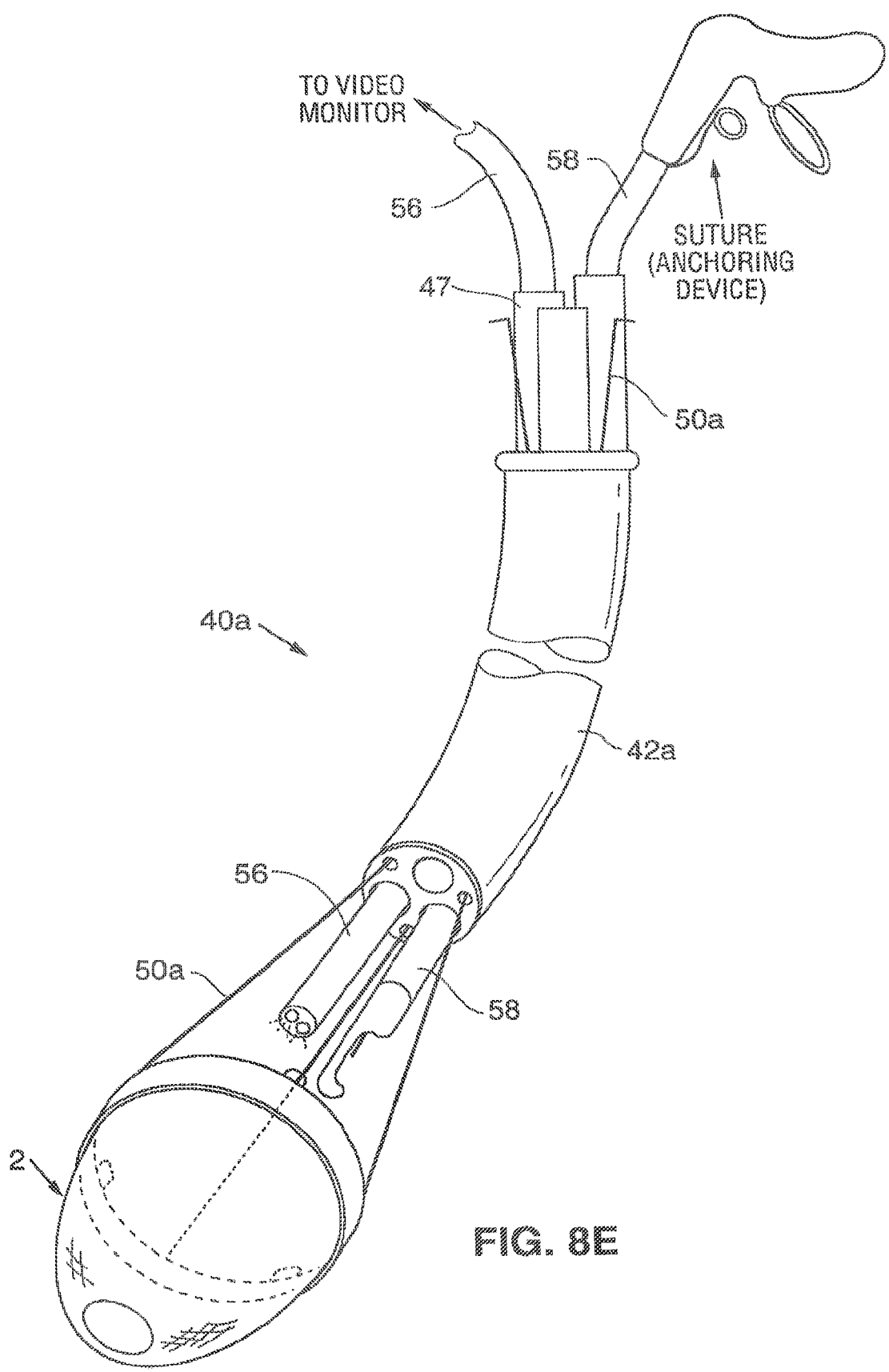
FIG. 8E is a perspective view of the variation of FIG. 8D.

In a modification to the second embodiment, shown in FIGS. 8D and 8E, positioning tool 40a includes an elongate sheath 42a. Slidable within the sheath is a cluster 43 of guide tubes 44a and instrument tubes 46a, preferably fixed in relation to one another. The proximal of end of each instrument tube 46a forms an instrument port 47 (FIG. 8E) that remains outside the body during use. Mandrels 50a extend through the guide tubes 44a and are temporarily attached to the pouch 2.

Cluster 43 may alternatively be a multi-lumen extrusion having lumens in place of guide tubes 44a and instrument tubes 46a.

Prior to use, the pouch 2 and the distal ends of the mandrels 50a are disposed within the sheath 42a, and sheath 42a is passed into the esophagus and advanced until the open distal end is disposed within the stomach. Next, the positioning mandrels 50a are advanced to expel the pouch from the open end of the sheath 42a and to open the pouch to its expanded position as shown in FIGS. 8D and 8E.

An endoscope 56 is passed through an instrument port 47 (FIG. 8E) at the proximal end of the tool 40a and advanced into the stomach. The mandrels are manipulated under endoscopic visualization to position the proximal portion of the pouch at the desired attachment location. The mandrels may be moved proximally or distally to adjust the proximal/distal location of the implant. The mandrels may be moved simultaneously, or they may be moved independently to adjust the angle of the implant to match the anatomy of the attachment location.

Once the pouch is visually confirmed to be in an appropriate orientation for fixation, an attachment device 58 such as the suture device shown in FIG. 8E is passed into an instrument port 47 and extended through an instrument tube 46a. The attachment device is used to apply fasteners such as sutures, staples, clips, adhesive etc. to secure the pouch 2 to the surrounding tissue. The attachment device 58, endoscope 56, and any other instruments passed through instrument ports 47 may be articulated using separate articulating components provided on the instruments themselves, or by articulating the cluster 43 itself using wire or other articulating components that may be actuated from outside the body.

Once the pouch is positioned, the mandrels are detached from the pouch and the mandrels are withdrawn. The endoscope and any remaining instruments are removed from the instrument lumens 46a, and the sheath 42a is withdrawn from the patient, leaving the pouch positioned within the stomach.

Third Embodiment

The third embodiment of a positioning tool 60 is similar to the first embodiment in that it utilizes a similar arrangement of a handle 62, slide member 64, cannula 66 and advancement mandrel 68. Mandrel 68 is coupled to an array of spring members 69 having a pre-formed arcuate shape as shown in FIG. 9A. Spring members 69 are temporarily attached to a pouch 2 as shown in FIG. 9A using sutures or the like.

For insertion of the pouch 2 into the body, slide member 64 is withdrawn in the proximal direction, thereby causing mandrel 68 to pull spring members 69 in a proximal direction and into the cannula 66. The pouch 2 may be packaged within a sheath (not shown but see sheath 38 of FIG. 3) to provide a more streamlined profile for insertion through the esophagus.

The distal end of the positioning tool 60 is passed through the esophagus and into the stomach. The slide 64 member is advanced in the distal direction, causing the mandrel 16 to extend the spring members 69 from cannula 66 and to spring into their natural curved orientations, thereby expanding the pouch. The handle 62 is manipulated while the pouch location is monitored endoscopically to position the pouch at the attachment location. With the pouch at the attachment location, the sheath (if any) is removed and the pouch is fixed to the surrounding tissue using sutures, clips, staples etc. secured through anchor loops 9 (FIG. 6) or directly through the walls of the pouch. Spring members 69 are then snipped free of the pouch 2 and are withdrawn into the cannula 66. The cannula 66 is withdrawn from the tissue, leaving the pouch 2 in place.

Fourth Embodiment

In a fourth embodiment, shown in FIGS. 10A and 10B, positioning tool 70 uses an inflatable balloon 72 as the expansion structure for the pouch. The balloon may be formed of elastic or inelastic materials, including silicone, polyurethane or other suitable materials. Balloon 72 is mounted to the distal end of a hollow cannula 76, and the a pouch 2 is temporarily attached to the exterior of the balloon 72 using sutures 74 or other detachable fasteners. Cannula optionally include an atraumatic distal tip 77 that may protrude out the distal opening 6 of the pouch 2 as in prior embodiments, or that may be disposed within the pouch 2 as shown.

Cannula 76 extends longitudinally from a handle 78. A source of inflation medium is fluidly coupled to the cannula by an inflation lumen (not shown) extending through the handle 78. Inflation medium flows into balloon 72 from an exit port 79 disposed within the balloon.

For insertion, the un-inflated balloon 72 and the pouch 2 may be packaged within a sheath as described previously. After the distal end of the positioning tool 70 and the pouch are inserted into the stomach, the sheath is removed and the balloon 72 is inflated to expand the pouch. The tool is withdrawn to draw the pouch into the desired attachment location, and it is visually confirmed that the circumference of the pouch is in contact with the surrounding tissue. Alternatively, the pouch may be positioned at the attachment location prior to inflation of the balloon. Under this alternative, the balloon expands the pouch into contact with the surrounding tissue.

Fine tuning of the pouch position is achieved by manipulating the positioning mandrel. Once the pouch is properly positioned, it pouch is secured to the surrounding tissue. The pouch is disconnected from the balloon 72, and the positioning tool 70 is then withdrawn from the patient's body.

Fifth Embodiment

Figure 11:
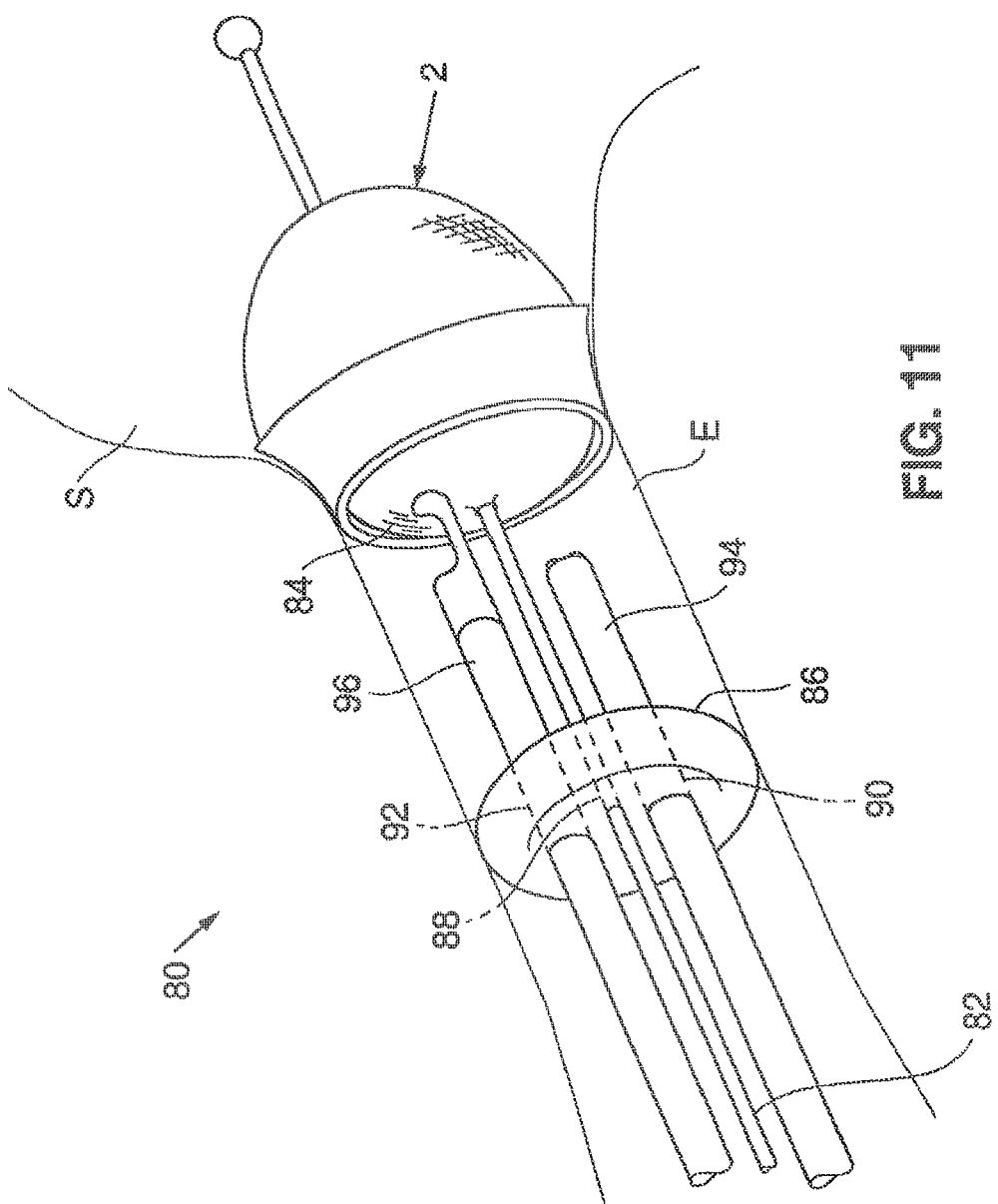
FIG. 11 is a perspective view showing a sixth embodiment of a positioning tool during use.

FIG. 11 shows a fifth embodiment of a positioning tool 80 which is similar to the fourth embodiment in that it includes an elongate cannula 82 carrying an inflatable distal expansion balloon 84. A proximal handle (not shown but see handle 78 of FIG. 10A) is attachable to a source of inflation medium for inflating the balloon 84. As with the fourth embodiment, the pouch 2 is attached either directly to the balloon 84 or to anchoring devices prior to implantation, and is inflated to expand the pouch.

The positioning tool 80 of the fifth embodiment differs from that of the fourth embodiment in that it includes a guide balloon 86 that is positionable over the cannula 82 as shown in FIG. 11. Guide balloon 86 includes a central channel 88 for receiving the cannula 82, as well as adjacent channels 90, 92 for receiving additional tools such as an endoscope 94 and a suturing device 96 that are required for placement of the implant. The relative positions of the channels 88, 90, 92 are selected to allow the positioning mandrel, endoscope, and attachment device to be arranged (relative to one another and to the pouch) in a manner which helps to center the pouch and tools within the operative area, which minimizes interference between the tools, which facilitates access to the attachment points using the attachment device, and which provides optimal visualization using the endoscope. Guide balloon 86 also includes an inflation tube that is not shown in FIG. 11.

The guide balloon 86 may be fixed to the cannula 82 or slidable on the cannula surface. If slidable, it may be provided as a permanent component of the positioning mandrel, or it may be provided as a separate component that can be added to the positioning mandrel, such as by briefly removing the proximal handle (see handle 78 of the FIG. 10A embodiment) to allow the balloon to be threaded onto the cannula. Materials useful for both of the balloons include elastic or inelastic materials suitable for use within the body.

During use of the fifth embodiment, the positioning mandrel, with the pouch 2 thereon, is inserted through the esophagus and into the stomach. The guide balloon 86 is positioned within the esophagus, preferably during or after insertion of the pouch into the stomach. The guide balloon 86 and expansion balloon 84 are inflated, either independently or simultaneously.

Endoscope 94 and attachment device 96 are extended through the channels 90, 92. The pouch 2, which has been expanded by the inflation of balloon 84, is moved into proper implantation position by manipulating the mandrel 82, and the pouch is secured in the proper position using the attachment device 96. As with each of the prior embodiments, these positioning and attaching steps are preferably performed under visualization using the endoscope.

If an impermeable seal between the pouch 2 and the surrounding tissue is desired (and if the instruments passed through the guide balloon 86 are in sealing contact against its channels 88, 90, 92), the patency of the seal may be checked before the pouch is fixed in place. This may be done by passing insufflation gas into the space between the guide balloon 86 and expansion balloon 84 and evaluating whether the gas is passing around the pouch and into the stomach.

If necessary, the guide balloon 86 may be rotated within the esophagus to change the rotational positions of the attachment device 96 and guide balloon 86. At the end of the procedure, the pouch is detached from the balloon 84, the balloon 84 and guide balloon 86 are deflated, and all components are removed from the body, leaving the pouch within the stomach.

A guide balloon similar to the balloon 88 of the fifth embodiment may be provided with various others of the described embodiments to facilitate centering and/or tool placement.

Sixth Embodiment

Figure 12:
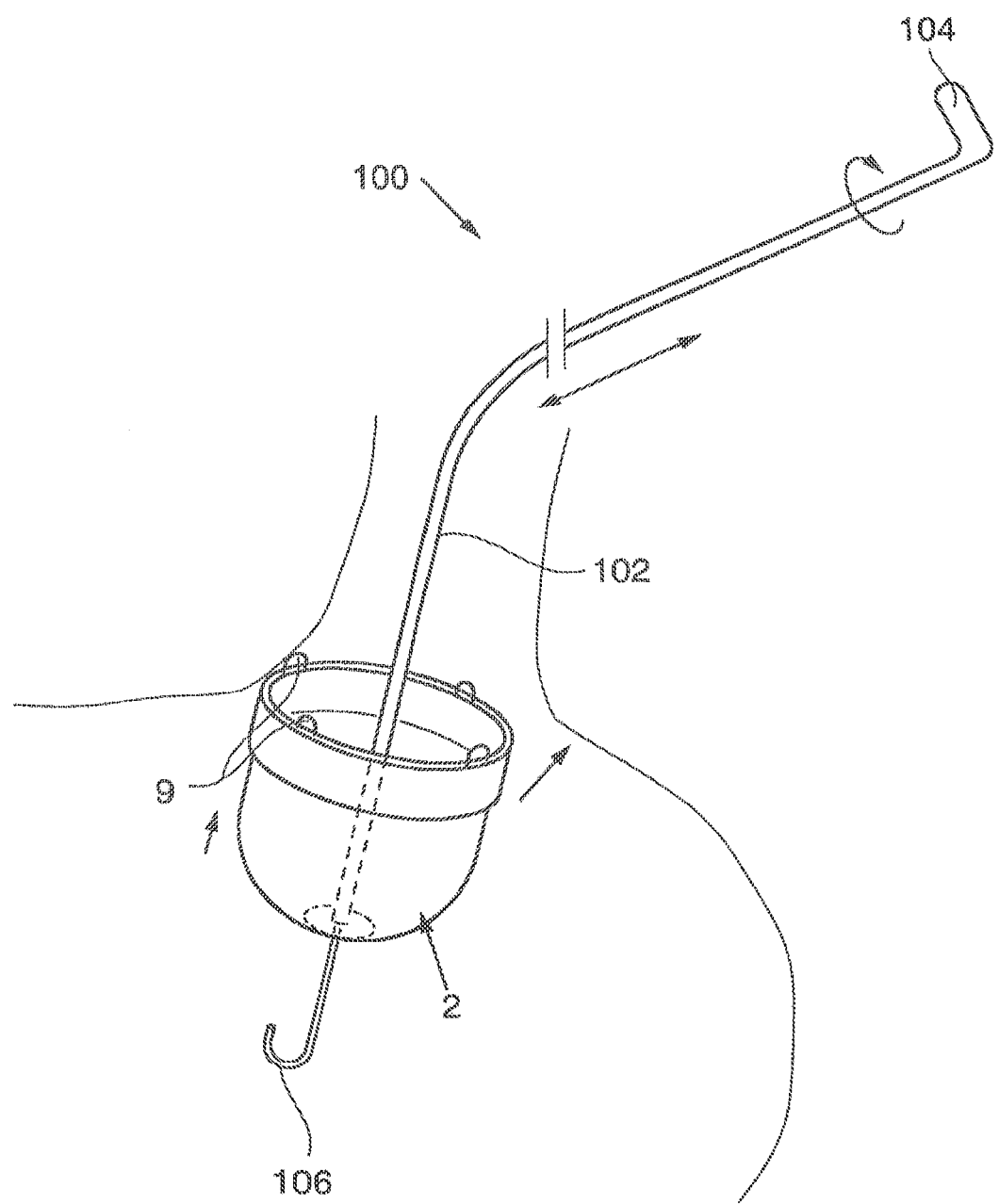
FIG. 12 is a schematic illustrating showing a seventh embodiment of a positioning tool during use.

FIG. 12 shows a sixth embodiment of a positioning tool 100. One aspect in which tool 100 differs from prior embodiments is in its lack of an active expansion mechanism at its distal end. Tool 100 includes an elongate mandrel 102 having a control handle 104 positionable outside of the body. Pouch 2 is temporarily attached to the distal end of the tool using detachable or self-releasing attachment means. Mandrel 102 may (optionally) be of sufficient length to extend through the distal opening 6 of pouch 2, forming a distal guide member with an atraumatic tip 106 that provides tactile guidance to the physician during advancement of the mandrel into the esophagus and stomach.

During use, mandrel 102 is used to direct the pouch 2 through the oral cavity and esophagus and into the proximal stomach. In one method, the mandrel with the pouch on its distal end may be positioned within a sheath (not shown), and the distal end of the sheath passed through the esophagus and into the stomach. The sheath and/or mandrel are manipulated to release the pouch 2 from the sheath, preferably at a desired attachment location. If the pouch is self-expandable, release of the pouch from the sheath will cause the pouch to self-expand, preferably (but optionally) into contact with the surrounding walls of the proximal stomach. This positioning step may be performed under visualization using an endoscope passed through the esophagus and into the region of interest.

If repositioning of the pouch 2 is needed, the control handle 104 of the mandrel is manipulated (e.g. rotated, advanced, retracted, pivoted) to move the pouch to a desired position and orientation. Next, the pouch is anchored to neighboring tissue as described above. The pouch is released from the mandrel. The mandrel and any other tools are withdrawn from the body. Various embodiments of positioning tools have been described herein. These embodiments are given by way of example and are not intended to limit the scope of the present invention. It should be appreciated, moreover, that the various features and steps of the embodiments that have been described may be combined in various ways to produce numerous additional embodiments and methods. Moreover, while various materials, dimensions, shapes, implantation locations, etc. have been described for use with disclosed embodiments, others besides those disclosed may be utilized without exceeding the scope of the invention.

It is claimed:

1. A device for positioning an implant in a patient, comprising:
   a handle;
   a cannula extending distally from the handle, wherein the cannula includes a fixed bent portion;
   a mandrel, at least a portion of the mandrel positioned within a lumen of the cannula, wherein the mandrel is flexible and configured to slide proximally and distally within the fixed bent portion of the cannula; and
   a plurality of expansion elements, each expansion element including a proximal portion and a distal portion, wherein the proximal and distal portions are pivotally connected to each other, and wherein a proximal end of the proximal portion and a distal end of the distal portion are movable relative to each other;
   wherein movement of the mandrel relative to the cannula corresponds to: a) movement of the proximal end of the proximal portion and the distal end of the distal portion of each expansion element towards each other, and b) a radially outward movement of a central portion of each expansion element.

2. The device of claim 1, wherein the proximal end of the proximal portion of each expansion element is pivotally coupled to the cannula, and the distal end of the distal portion of each expansion element is pivotally coupled to the mandrel.

3. The device of claim 1, wherein an exterior of the handle includes a sliding member coupled to the mandrel.

4. The device of claim 1, wherein the mandrel extends distally past a distal end of the cannula.

5. The device of claim 1, wherein movement of the mandrel relative to the cannula is movement of the mandrel proximally relative to the cannula, and movement of the mandrel distally relative to the cannula corresponds to: a) movement of the proximal end of the proximal portion and the distal end of the distal portion of each expansion element away from each other, and b) a radially inward movement of the central portion of each expansion element.

* * * * *